(12) United States Patent
Won et al.

(10) Patent No.: US 10,898,582 B2
(45) Date of Patent: Jan. 26, 2021

(54) BI-FUNCTIONAL ALLOSTERIC PROTEIN-DRUG MOLECULES FOR TARGETED THERAPY

(71) Applicant: UNIVERSITY OF UTAH RESEARCH FOUNDATION, Salt Lake City, UT (US)

(72) Inventors: Youngwook Won, Salt Lake City, UT (US); David A. Bull, Salt Lake City, UT (US); Kwangsuk Lim, Seoul (KR)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 277 days.

(21) Appl. No.: 15/534,948

(22) PCT Filed: Dec. 11, 2015

(86) PCT No.: PCT/US2015/065308
§ 371 (c)(1),
(2) Date: Jun. 9, 2017

(87) PCT Pub. No.: WO2016/094831
PCT Pub. Date: Jun. 16, 2016

(65) Prior Publication Data
US 2017/0368196 A1 Dec. 28, 2017

Related U.S. Application Data

(60) Provisional application No. 62/090,760, filed on Dec. 11, 2014.

(51) Int. Cl.
| | | |
|---|---|---|
| *A61K 47/68* | (2017.01) | |
| *C07K 16/32* | (2006.01) | |
| *A61K 9/00* | (2006.01) | |
| *A61K 31/27* | (2006.01) | |
| *A61K 31/337* | (2006.01) | |

(52) U.S. Cl.
CPC ........ *A61K 47/6855* (2017.08); *A61K 9/0019* (2013.01); *A61K 31/27* (2013.01); *A61K 31/337* (2013.01); *A61K 47/6801* (2017.08); *A61K 47/6803* (2017.08); *A61K 47/6849* (2017.08); *A61K 47/6879* (2017.08); *A61K 47/6889* (2017.08); *C07K 16/32* (2013.01); *C07K 2317/622* (2013.01); *C07K 2319/33* (2013.01)

(58) Field of Classification Search
CPC ............ C07K 2319/33; C07K 2319/70; A61K 47/6889
See application file for complete search history.

(56) References Cited

U.S. PATENT DOCUMENTS

| | | |
|---|---|---|
| 5,106,951 A | 4/1992 | Morgan, Jr. et al. |
| 5,252,713 A | 10/1993 | Morgan, Jr. et al. |
| 8,142,784 B2 | 3/2012 | Ebens, Jr. et al. |
| 2005/0256097 A1 | 11/2005 | Zhong et al. |
| 2006/0018911 A1 | 1/2006 | Ault-Riche et al. |
| 2014/0072586 A1 | 3/2014 | Morrison et al. |
| 2016/0106858 A1* | 4/2016 | Hall ...................... C07K 16/18 424/450 |

FOREIGN PATENT DOCUMENTS

| | | |
|---|---|---|
| WO | WO-95/03064 A1 | 2/1995 |
| WO | WO-2005/014823 A2 | 2/2005 |
| WO | WO-2007/137117 A2 | 11/2007 |
| WO | WO-2008/115805 | 9/2008 |
| WO | WO-2010/065969 | 6/2010 |
| WO | WO-2015/148126 A1 | 10/2015 |
| WO | WO-2016/094831 | 6/2016 |

OTHER PUBLICATIONS

Dean et al, Journal of Lipid Research, 2001, vol. 42, pp. 1007-1017) (Year: 2001).*
Kilic et al (Frontiers in Bioscience, 2006, vol. 11, pp. 1716-1721) (Year: 2006).*
Yuno et al, 'Clinical Evaluation and Biomarker Profiling of Hsp90 Inhibitors', In: Chaperones: Methods and Protocols, Methods in Molecular Biology, 2018, pp. 423-441 (Year: 2018).*
Jordan and Wilson, Nature Reviews Cancer, 2004, vol. 4, pp. 253-265 (Year: 2004).*
Extended European Search Report dated Jul. 16, 2018 by the European Patent Office for Patent Application No. 15866523.2, which was filed on Dec. 11, 2015 and published as EP 3230322 on Oct. 18, 2017 (Inventor—Won et al.; Applicant—University of Utah research Foundation; (6 pages).
Grover AS, "Use of Allosteric Targets in the Discovery of Safer Drugs",(2013); Med Princ Pract. 22(5):418-26.
Snyder J.P., et al., "The binding conformation of Taxol in β-tubulin: A model based on electron crystallographic density", (2001); PNAS 98(9): 5312-5316.
Won, Y.W., et al., "Oligopeptide complex for targeted non-viral gene delivery to adipocytes", (2014); Nature Materials 13, 1157-1164.
International Search Report and Written Opinion were dated Feb. 19, 2016 by the International Searching Authority for International Application No. PCT/US2015/065308, which was filed on Dec. 11, 2015 and published as WO 2016/094831 on Jun. 16, 2016 (Applica— University of Utah Research Foundation) (10 pages).

(Continued)

*Primary Examiner* — Karen A. Canella
(74) *Attorney, Agent, or Firm* — Ballard Spahr LLP

(57) ABSTRACT

Disclosed herein, is a bi-functional allosteric protein-drug molecule comprising a targeting moiety, one or more biological binding domains, and one or more therapeutic agents, wherein the therapeutic agent is allosterically bound to the biological binding domain. Also described herein, are methods of incorporating a bi-functional allosteric protein-drug molecule comprising a targeting moiety, one or more biological binding domains that captures the therapeutic agent without the formation of a chemical bond, and one or more therapeutic agents; physiologically acceptable compositions including them; and methods of administering the bi-functional allosteric protein-drug molecule to patients for the treatment of cancer.

19 Claims, 26 Drawing Sheets

(56) References Cited

OTHER PUBLICATIONS

International Preliminary Report on Patentability was dated Jun. 13, 2017 by the International Searching Authority for International Application No. PCT/US2015/065308, which was filed on Dec. 11, 2015 and published as WO 2016/094831 on Jun. 16, 2016 (Applicant—University of Utah Research Foundation) (8 pages).

Communication pursuant to Article 94(3)EPC was dated Jun. 26, 2019 by the European Patent Office for EP Application No. 15866523.2, which was filed on Jul. 11, 2017 and published as EP 3230322 A1 on Oct. 18, 2017 (Applicant-21101—Univ. of Utah Research Foundation) (4 pages).

* cited by examiner

BI-FUNCTIONAL ALLOSTERIC PROTEIN-DRUG MOLECULES FOR TARGETED THERAPY

CROSS-REFERENCE TO RELATED PATENT APPLICATIONS

This application claims the benefit of priority under 35 U.S.C. § 371 of International Application No. PCT/US2015/065308 filed on Dec. 11, 2015 which claims priority to U.S. Provisional Application No. 62/090,760 filed on Dec. 11, 2014. The content of these earlier filed applications is hereby incorporated by reference in their entirety.

BACKGROUND

Cancer is one of the leading causes of death in the world. Despite improvements in prevention, early detection, treatment and survival, the American Cancer Society states that breast cancer is the second most common newly diagnosed cancer and second leading cause of death among women in the United States. Targeted therapy is one treatment option available to patients involving the administration of drugs such as antibodies that are selective for cancer cells leaving normal cells relatively unharmed. Conventional antibody-drug conjugate technology for breast cancer is limited in large part because the low concentration of antibody present in antibody-drug molecules are conjugated through a synthetic linker. Further limitations include one or more of the following: high production cost, inherent immunogenicity, multiple steps required for conjugation; and/or safety issues related to the synthetic linker. Alternative approaches are needed for improving the construction of antibody-drug complexes for targeted disease therapy.

SUMMARY

Disclosed herein, are bi-functional allosteric protein-drug molecules comprising a targeting moiety, one or more biological binding domains, and one or more therapeutic agents, wherein the therapeutic agent is allosterically bound to the biological binding domain.

Disclosed herein, are pharmaceutical compositions comprising bi-functional allosteric protein-drug molecules comprising a targeting moiety, one or more biological binding domains, and one or more therapeutic agents, wherein the therapeutic agent is allosterically bound to the biological binding domain, and a pharmaceutically acceptable carrier.

Disclosed herein, are methods of treating a patient with cancer, the method comprising (a) identifying a patient in need of treatment; and (b) administering to the patient a therapeutically effective amount of a pharmaceutical composition comprising a bi-functional allosteric protein-drug molecule comprising a targeting moiety, one or more biological binding domains, and one or more therapeutic agents, wherein the therapeutic agent is allosterically bound to the biological binding domain, and a pharmaceutically acceptable carrier. Any of the methods of treatment can be configured as methods of "use."

Other features and advantages of the present compositions and methods are illustrated in the description below, the drawings, and the claims.

DETAILED DESCRIPTION

Figure 1:
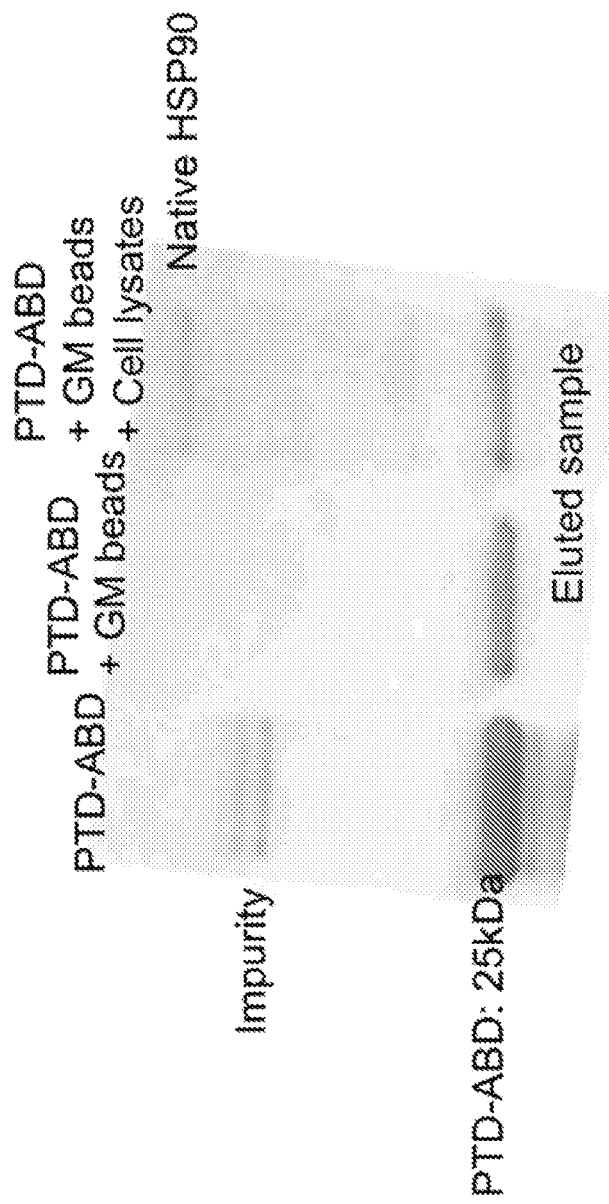
FIG. 1 is a picture of an SDS-PAGE of the eluted samples: the protein transduction domain-ATP binding domain (PTD-ABD) (left lane); the PTD-ABD captured by geldanamycin (GM) beads (middle lane); and the addition of cell lysate to the PTD-ABD+GM beads (right lane).

The present disclosure can be understood more readily by reference to the following detailed description of the invention, the figures and the examples included herein.

Before the present compositions and methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Moreover, it is to be understood that unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, and the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

Definitions

As used in the specification and the appended claims, the singular forms "a," "an" and "the" include plural referents unless the context clearly dictates otherwise.

The word "or" as used herein means any one member of a particular list and also includes any combination of members of that list.

Ranges can be expressed herein as from "about" or "approximately" one particular value, and/or to "about" or "approximately" another particular value. When such a range is expressed, a further aspect includes from the one particular value and/or to the other particular value. Similarly, when values are expressed as approximations, by use of the antecedent "about," or "approximately," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

As used herein, the terms "optional" or "optionally" mean that the subsequently described event or circumstance may or may not occur and that the description includes instances where said event or circumstance occurs and instances where it does not.

As used herein, the term "sample" is meant a tissue or organ from a subject; a cell (either within a subject, taken directly from a subject, or a cell maintained in culture or from a cultured cell line); a cell lysate (or lysate fraction) or cell extract; or a solution containing one or more molecules derived from a cell or cellular material (e.g. a polypeptide or nucleic acid), which is assayed as described herein. A sample may also be any body fluid or excretion (for example, but not limited to, blood, urine, stool, saliva, tears, bile) that contains cells or cell components.

As used herein, the term "subject" refers to the target of administration, e.g., a human. Thus the subject of the disclosed methods can be a vertebrate, such as a mammal, a fish, a bird, a reptile, or an amphibian. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.). In one aspect, a subject is a mammal. In another aspect, a subject is a human. The term does not denote a particular age or sex. Thus, adult, child, adolescent and newborn subjects, as well as fetuses, whether male or female, are intended to be covered.

As used herein, the term "patient" refers to a subject afflicted with a disease or disorder. The term "patient" includes human and veterinary subjects. In some aspects of the disclosed methods, the "patient" has been diagnosed with a need for treatment for cancer, such as, for example, prior to the administering step.

As used herein, the term "bi-functional allosteric protein-drug molecule" refers to a composition comprising a bi-functional allosteric protein and one or more therapeutic agents, wherein the therapeutic agent is allosterically bound to the biological binding domain of the bi-functional allosteric protein. An example of a bi-functional allosteric protein-drug molecule can be, for instance, "scFv-TBD-PTX" indicating a single chain antibody bound to a taxane binding domain which is then allosterically bound to paclitaxel (a drug molecule).

The bi-functional allosteric protein-drug molecules described below have the following advantages over other known antibody-drug conjugates: 1) one or more biological binding domains that capture one or more therapeutic agents without the formation of a chemical bond, thus avoiding over-conjugation of the antibody-drug conjugate; 2) one or more therapeutic agents that minimize the presence of free antibody; and 3) can enhance half-life in the circulation while retaining affinity to an antigen.

As used herein, the term "bi-functional allosteric protein" refers to a protein comprising a targeting moiety and one or more biological binding domains. Examples of bi-functional allosteric proteins include, but are not limited to, bi-functional recombinant scFv-ABD (ATP binding domain) fusion proteins, recombinant scFv-ABD and scFv fusion proteins. In some aspects, a bi-functional allosteric protein can comprise one or more biological binding domains. For example, disclosed herein are bi-functional allosteric proteins comprising an anti-HER2 antibody targeting moiety and one or more biological binding domains, such as ATP, that then can allosterically bind or capture one or more therapeutic agents, such as 17-allyaminogeldanamycin (17-AGG).

As used herein, the term "targeting moiety" refers to the portion of the bi-functional allosteric protein that specifically binds a selected target. The targeting moiety can be, for example, an antibody, peptide, polypeptide, growth factor or any ligand protein. The target can be, for example, a receptor or an antigen (e.g., HER2 (also called ErbB-2, ERBB2) or EGFR).

As used herein, the term "biological binding domain" or "binding domain" refers to the portion of the bi-functional allosteric protein that can allosterically bind to or capture a therapeutic agent without the creation of chemical bonds. "Binding domain" or "BD" can be an "ATP Binding Domain" or "ABD", respectively.

Bi-Functional Allosteric Protein-Drug Molecules
Targeting Moiety.

In some aspects, the targeting moiety of the bi-functional allosteric protein-drug molecule can be a protein, including but not limited to a peptide or polypeptide, an antibody or biologically active variant thereof, growth factor or other ligand protein. For example, if the targeting moiety is an antibody, the antibody can be a single chain antibody (scFv) or a Fab fragment; a human, chimeric or humanized antibody or a biologically active variant thereof and/or can be (or can be derived from) a monoclonal or polyclonal antibody. The antibody can be a naturally expressed antibody (e.g., a tetrameric antibody) or a biologically variant thereof.

In some aspects, the targeting moiety of the bi-functional allosteric protein-drug molecule can be a non-naturally occurring antibody (e.g., a single chain antibody or diabody) or a biologically active variant thereof. As noted above, the variants include, without limitation, a fragment of a naturally occurring antibody (e.g., an Fab fragment), a fragment of a scFv or diabody, or a variant of a tetrameric antibody, an scFv, a diabody, or fragments thereof that differ by an addition and/or substitution of one or more amino acid residues. The antibody can also be further engineered.

In other aspects, bi-functional allosteric protein-drug molecules, described herein, comprise a targeting moiety, wherein the targeting moiety is a scFv or Fab fragment that binds to a growth factor receptor. The growth factor receptor can be a receptor bound by a member of the epidermal growth factor (EGF) family. Examples of receptors for proteins in the EGF family include an EGF receptor (EGFR), a heparin-binding EGF-like growth factor receptor (HB-EGFR), an amphiregulin receptor (AR), an epiregulin receptor (EPR), a betacellulin receptor, and a receptor for neuregulin (e.g., a receptor for neuregulin-1, neuregulin-2, neuregulin-3, or neuregulin-4). Accordingly, in some embodiments, the growth factor receptor is a member of the EGFR family (e.g., HER2 (human epidermal growth factor receptor 2), sometimes called ERBB2, HER2/neu) and the targeting moiety is an antibody, including, but not limited to, trastuzumab, cetuximab, or panitumumab, or a biologically active variant thereof. In some aspects, the scFv or Fab fragment can bind a cell surface receptor, or a cell membrane protein (e.g., transport proteins, membrane enzymes, and cell adhesion molecules). Other suitable targets to which a "targeting moiety" can bind, include without limitation, hormone receptors (e.g., estrogen, progesterone), cytokine receptors (i.e., type I, such as growth hormone receptor, prolactin, erythropoietin; type II; members of the immunoglobulin superfamily, such as interleukin-1; tumor necrosis factor receptor family, such as CD27, CD30, CD40; chemokine receptors, such as interleukin-8, CCR1, CXCR4; transforming growth factor (TGF) beta receptors); cell adhesion molecules (e.g., integrin); and vascular endothelial growth factor (VEGF) receptors (e.g., neurophilin (NRP) receptors, such as NRP1, NRP2). More generally, the targeting moiety can be a therapeutic agent, such as an anti-cancer agent (e.g., trastuzumab, cetuximab) or an anti-inflammatory agent.

Biological Binding Domain.

Disclosed herein are bi-functional allosteric protein-drug molecules comprising a targeting moiety, one or more biological binding domains, wherein the biological binding domain comprises an ATP binding domain and/or a taxane binding domain, and one or more therapeutic agents, wherein the therapeutic agent is allosterically bound to the biological binding domain. The biological binding domain disclosed herein, can be any molecule, compound, enzyme or nucleic acid capable of forming an allosteric binding pocket. The disclosure features, for example, one of more of the biological binding domains capable of allosterically binding to one or more therapeutic agents. The biological binding domain can be selected based on its ability to form a binding pocket to permit the capture of one or more therapeutic agents via allosterically binding. Examples of one or more therapeutic agents to which a biological binding domain can be selected include without limitation are monomethyl auristatin E (MMAE), calicheamicins (e.g., calicheamicin gamma1, enediyne esperamicin), maytansine (also referred to as maitansine), doxorubicin (also referred to as Adriamycin®, Myocet®, Rubex®; also known as hydroxydaunorubicin, hydroxydaunocycin), camptothecin and/or duocarmycins, including synthetic analogs adozelesin, bizelesin, and carzelesin; and any derivatives or analogues thereof. The biological binding domain can also be therapeutic agent and/or have therapeutic properties, such as, ATP, for example.

The disclosure further features bi-functional allosteric protein-drug molecules as described herein comprising two or more biological binding domains that are different (i.e., the biological binding domains of a single bi-functional allosteric protein-drug molecule can be a combination of more than one type of biological binding domain). Such bi-functional allosteric protein-drug molecules, comprising more than one type of biological binding domains, can capture different types of therapeutic agents in a single formulation, and thus, can deliver different therapeutic agents. For example, a bi-functional allosteric protein-drug molecule comprising an ATP binding domain and a taxane binding domain can capture and thus deliver 17-AAG and paclitaxel, respectively. Also, the bi-functional allosteric protein-drug molecules described herein can comprise two or more biological binding domains that are the same but are allosterically bound to different therapeutic agents.

Therapeutic Agents.

A wide variety of therapeutic agents or cytotoxic agents can be incorporated into the bi-functional allosteric protein-drug molecule. The therapeutic agents or cytotoxic agents can be a chemical compound or a protein. In some aspects, one or more of the therapeutic agents can be an anti-cancer agent. The anti-cancer agent can be an agent or drug that has anti-cancer properties. In some embodiments, the anti-cancer agent can be a derivative of geldanamycin (a naturally occurring ansamycin antibiotic), a taxane or a heat shock protein 90 (HSP90) inhibitor. Examples of geldanamycin derivatives include but are not limited to 17-allylamino-17-demethoxygeldanamycin (17-AAG), 17-dimethylaminoethylamino-17-demethoxygeldanamycin (17-DMAG) or any analogues thereof. Examples of a taxane include but are not limited to paclitaxel and docetaxel and any analogues thereof. Examples of HSP90 inhibitors include but are not limited to geldanamycin, geldanamycin derivatives (17-DMAG), radicicol (also called monorden), retaspimycin hydrochloride (also known as IPI-504), non-ansamycin compounds (BIIB021), SNX-5422 (PF-04929113), ganetespib (also known as STA-9090) and NVP-AUY922. The anti-cancer agent can also be an EGFR inhibitor. Examples of EGFR inhibitors include but are not limited to erlotinib (Tarceva®) and afatinib (Gilotrif®).

The bi-functional allosteric protein-drug molecules disclosed herein can be a therapeutic agent including but not limited to one or more molecular chaperone inhibitors (e.g., a HSP90 inhibitor), or tublin inhibitors (e.g., taxane) and/or stabilizers or DNA replication inhibitors or any anti-cancer agent or any derivatives and/or analogues thereof to provide an additional therapeutic benefit.

Cytotoxins that target microtubules include, without limitation, the taxanes, and in particular, the taxanes including, paclitaxel (Taxol®), docetaxel (Taxotere®), and cabazitaxel (Jevtana®). Nontaxane microtubule-targeting agents such as an epothilone (e.g., epothilone A, B, C, D, E, or F) and eribulin can also be incorporated. Other useful cytotoxic agents include the alkaloids (e.g., a vinca alkaloid such as vincristine, vinblastine, vindesine, and vinorelbine), an alkylating agent (e.g., cyclophosphamide, mechlorethamine, chlorambucil, or melphan) an anthracycline (e.g., daunorubicin, doxorubicin, epirubicin, idarubicin, mitoxantrone, and valrubicin), an auristatin (e.g. monomethyl auristatin E (MMAE), an antifolate (e.g., methotrexate or aminopterin), a calicheamicin (e.g., calicheamicin y 1), a duocarmycin (e.g., adozelesin, bizelesin, or carzelesin); a mitomycin (e.g., mitomycin C), a pyrimidine analog (e.g., fluorouracil), or a derivative of mytansine (e.g., a mytansinoid such as ansamitocin, mertansine, or emtansine).

Linker-Free Technology

Although advances in linker technology have led to the production of highly potent antibody-drug conjugates with enhanced stability in the bloodstream, which in turn has improved the targeted delivery of cytotoxic agents, they still have limited clinical use because of poor therapeutic efficacy in human patients. These limitations include antibody accumulation in normal tissues, immunogenicity and difficulties in the chemical conjugation of cytotoxic drugs to the required antibody. In addition, cytotoxins have limited therapeutic use in cancer patients because of their toxicity profiles. Factors that limit the number of drug molecules delivered into cancer cells include the small number of antigens present on the cell surface; the rate of internalization of the antibody-drug conjugate; and intracellular processing to release the drug from the antibody. Further, several steps are involved beginning from the administration of the antibody-drug conjugate to the release of the drug (or cytotoxic agent) in cancer cells. These steps include: 1) the antibody-drug conjugate reaching the tumor; 2) binding of the antibody-drug conjugate to the surface of the cell; 3) internalization of the antibody-drug conjugate; 4) cleavage of the linker; 5) endolysosomal escape; and 6) the drug reaching its intra-cellular target.

Disclosed herein, are compositions comprising bi-functional allosteric protein-drug molecules and methods of making said molecules using linker-free technology. For example, one or more of the therapeutic agents are incorporated into the biological binding domain spontaneously without altering the structure or activity of the therapeutic agent or the affinity of the bi-functional allosteric protein (e.g., scFv), to its target (e.g., antigen). In other words, the formation of the bi-functional allosteric protein-drug molecules described herein relies on the biological binding affinity of the therapeutic agent (e.g., anti-cancer agent) and does not require chemical conjugation to join molecules. Accordingly, in some aspects, the bi-functional allosteric protein-drug molecule comprises a targeting moiety (e.g., recombinant scFv), one or more biological binding domains (e.g., ATP) and one or more therapeutic agents such that a single binding domain (e.g., ATP) captures a single therapeutic molecule (e.g., 17-AAG). The association of the biological binding domain and the therapeutic agent occurs because of the binding affinity of the therapeutic molecule (e.g., 17-AAG) to the binding domain (e.g., ATP). Another feature disclosed herein is that the incorporation of the therapeutic agent (e.g., 17-AAG) into the biological domain (for example, scFv-ABD), results in a bi-functional allosteric protein-drug molecule (e.g., scFv-ATP-17-AAG) that is ready to use. In some instances, the incorporation of the therapeutic agent into the biological domain can be within one hour of incubation.

Additional advantages of using linker-free technology compared to the drugs conjugated to an antibody with a synthetic linker are as follows. In current antibody-drug conjugate technologies, the optimum number of drug molecules is limited to 3 to 4 drug molecules per antibody. The bi-functional allosteric protein-drug molecule described herein can be homogenous and the number of therapeutic molecules incorporated into the bi-functional allosteric protein can be controlled by adding more biological binding domains. Moreover, the number of steps from administration to drug release listed above is reduced from six steps to four (e.g., steps 4 and 6 are omitted). And, other steps can be minimized (e.g., step 3). For example, the bi-functional allosteric protein (e.g., scFv) is smaller than the monoclonal antibody used in current antibody-drug conjugates and thus, facilitates its internalization into cancer cells and thereby minimizing the time for the therapeutic agent to reach its intracellular target. And, because the release of the therapeutic agent is driven by its inherent affinity for its target, chemical cleavage of a synthetic linker is not required. Further, when the therapeutic agent is a drug that targets a protein, for example, a cytosolic protein, that is important in cancer cell survival, such as 17-AAG, for instance, the therapeutic agent does not need to migrate into the nucleus and can exert its anti-cancer activity even in cancer cells that are not dividing. Accordingly, in some embodiments, the therapeutic agent is a drug that targets onco-proteins present in the cytosol. Because the methods of producing bi-functional allosteric protein-drug molecules, as disclosed herein, has fewer steps from administration to drug activity compared to antibody-drug conjugate therapies, more of the dose delivered can reach its target site to exert its anti-cancer activity. In some embodiments, the dose delivered to the target site can be more than 6-fold higher compared to current antibody-drug conjugate technologies.

The methods described herein can serve as a platform for the design of other binding domains to anchor other highly potent drugs to a targeting moiety without the need for a linker or other forms of chemical conjugation. Further, by using the platform described herein, chemotherapeutic agents currently in clinical use as well as therapeutic agents and cytotoxins are candidates for the development and/or production of bi-functional allosteric protein-drug molecules.

Methods of Making Bi-Functional Allosteric Protein-Drug Molecules

Disclosed herein are techniques that can be used to produce the bi-functional allosteric protein-drug molecules described herein.

Bi-Functional Allosteric Proteins.

In some aspects, the scFv-ABD or the scFv-TBD disclosed herein is a recombinant fusion protein that is expressed in living cells (e.g., mammalian cells). Briefly, a plasmid DNA encoding the recombinant fusion protein, bound to one or more biologically binding domains (e.g., scFv-ABD or scFv-TBD), amino acid sequences is transfected into mammalian cells (e.g., HEK293 cells or CHO cells). The transfected cells are incubated to express the scFv-ABD or the scFv-TBD for at least a week or in some cases more than one week. After the incubation period, the cells are lysed and the whole protein is collected. The expressed scFv-ABD or the scFv-TBD is purified using a fast protein liquid chromatography (see Example 1). The purified protein, the scFv-ABD or the scFv-TBD, is then lyophilized and stored at −80° C. until use.

Bi-Functional Allosteric Protein-Drug Molecules.

Disclosed herein are methods of producing the bi-functional allosteric protein-drug molecule (e.g., scFv-ABD-17-AAG) comprising the following steps: (1) dissolving a bi-functional scFv-ABD in physiological buffer at a predetermined concentration; (2) dissolving 17-AAG in an appropriate solvent at a predetermined concentration; (3) mixing the solutions as a result of steps (1) and (2) at an optimized ratio, i.e., the ratio that yields the highest incorporation of a therapeutic agent into a bi-functional scFv-ABD; and (4) diluting the solution of step (3) in physiological buffer to make a final concentration for administration (e.g., infusion, injection). One of ordinary skill in the art can determine the proper solvent(s) required and calculate the concentrations of any of the ingredients involved in each step.

Antibodies.

As noted above, the bi-functional allosteric protein-drug molecules as disclosed herein, can include an antibody or a biologically active variant thereof. As is well known in the art, monoclonal antibodies can be made by recombinant DNA. DNA encoding monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques.

In vitro methods are also suitable for preparing monovalent antibodies. As it is well known in the art, some types of antibody fragments can be produced through enzymatic treatment of a full-length antibody. Digestion of antibodies to produce fragments thereof, particularly, Fab fragments, can be accomplished using routine techniques known in the art. For instance, digestion can be performed using papain. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross-linking antigen. Antibodies incorporated into the present bi-functional allosteric protein-drug molecules can be generated by digestion with these enzymes or produced by other methods.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment can be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment.

As used herein, the term "antibody" or "antibodies" can also refer to a human antibody and/or a humanized antibody. Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen binding portion of an antibody) which contains a portion of an antigen binding site from a non-human (donor) antibody integrated into the framework of a human (recipient) antibody.

The Fv region is a minimal fragment containing a complete antigen-recognition and binding site consisting of one heavy chain and one light chain variable domain. The three CDRs of each variable domain interact to define an antigen-biding site on the surface of the Vh-Vl dimer. Collectively, the six CDRs confer antigen-binding specificity to the antibody. As well known in the art, a "single-chain" antibody or "scFv" fragment is a single chain Fv variant formed when the VH and Vl domains of an antibody are included in a single polypeptide chain that recognizes and binds an antigen. Typically, single-chain antibodies include a polypeptide linker between the Vh and Vl domains that enables the scFv to form a desired three-dimensional structure for antigen binding.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies can also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody.

Methods for humanizing non-human antibodies are well known in the art. For example, humanized antibodies can be generated by substituting rodent CDRs or CDR sequences for the corresponding sequences of a human antibody. Methods that can be used to produce humanized antibodies are also well known in the art.

Biological Binding Domains.

The term "binding affinity" in the context of further describing the biological binding domain, refers to the interaction of a biological binding domain with a therapeutic agent. In general, the binding affinity of the biological binding domain to a therapeutic agent should be maintained at a level that promotes an interaction between the biological binding domain and a therapeutic agent that is stable in systemic circulation (i.e., the therapeutic agent remains allosterically bound to the biological binding domain in the presence of serum proteins), and facilitates the delivery or unloading of a therapeutic agent to its target (e.g., cancer cell). It can be this difference in the binding affinities of a therapeutic agent to serum proteins compared to a given target molecule in a cell that provides a mechanism for the release of a therapeutic agent from the biological binding domain in a cell. For example, the binding affinity of a therapeutic agent is generally greater for the biological binding domain compared to any serum protein, but low enough to permit its release once it reaches its target.

Assessment.

The bi-functional allosteric protein-drug molecules themselves or parts of the bi-functional allosteric protein-drug molecule can be assessed in any number of ways. For example, the binding of the therapeutic agent with the biological binding domain can be confirmed (by using a magnetic bead-based pull down assay); cellular or kinetic uptake of the therapeutic agent can be evaluated (using fluorescence techniques); levels of the unbound antibody and low levels of free drug can be confirmed (by gel separation and Western blotting), function of the biological binding domain as a reducer of cellular ATP and an inducer of apoptosis (by performing live/dead assay using FACS); the binding of, for example, scFv-ABD to different numbers of therapeutic molecules (by binding assays using a biotinylated GM probe); and for stability and tissue distribution in vivo (e.g., by measuring plasma levels over time and tissue distribution by imaging assays).

Configurations.

Each part of a given bi-functional allosteric protein-drug molecule, including the targeting moiety, biological binding domain and therapeutic agent, can be selected independently. One of ordinary skill in the art would understand that the component parts need to be associated in a compatible manner. The bi-functional allosteric protein-drug molecules can be used to deliver antibody moieties and therapeutic agents to a patient for the treatment of cancer. The targeting moiety can be referred to as a "first agent," the therapeutic called the "second agent" and the biological binding domain, referred to as a "third agent." And, thus, the bi-functional allosteric protein-drug molecules can be a combination therapy for a disease (e.g., a cancer). Different binding domains can carry different therapeutic agents. Thus, a bi-functional allosteric protein-drug molecule can deliver two or more different therapeutic agents. With the inclusion of a detectable marker, the bi-functional allosteric protein-drug molecule or the bi-functional allosteric protein as described herein can also be used to map the distribution of targets to which the targeting moieties bind. The number of therapeutic molecules per bi-functional allosteric protein (e.g., scFv) can be controlled by adding more binding domains. For example, more binding domains can be added to the C-terminus end of the bi-functional allosteric protein.

Accordingly, in some aspects, the biological binding domain can be two or more. In other embodiments, the biological binding domain and the therapeutic agent are present in a ratio of 1:1 (binding domain:therapeutic agent). The binding domain:therapeutic agent ratio can also be 2:2, 3:3, 4:4 or 5:5 or any other combination thereof. Each binding domain is capable of capturing a single therapeutic agent or drug molecule. For example, the one or more taxane binding domains can allosterically bind to one or more taxane molecules, in which the taxane molecules can be either the same or different. In some aspects, the biological binding domain can be different in a single formulation. Thus, the biological binding domains capture different therapeutic agents or drug molecules.

In addition, the biological binding domain (e.g., ATP) serves not only as a carrier of the therapeutic agent, but can also act as a therapeutic agent or possess one or more therapeutic properties (i.e., reduce cellular ATP levels). For instance, after the release of the therapeutic agent, the ATP binding domain can bind to ATP molecules in cancer cells, thereby leading to a decrease in cellular free ATP levels, cell cycle arrest, reduced proliferation, and/or apoptosis. Thus, the bi-functional allosteric protein-drug molecules described herein can be multi-functional and thus, the target delivery of, for example, an anti-cancer agent or molecular chaperone inhibitor, such as an HSP 90 inhibitor (e.g., 17-AAG) by the bi-functional allosteric protein-drug molecule can be a synergistic therapy for the treatment of disease, such as cancer (e.g., breast cancer). Also, the ATP biological binding domain can bind more than one type or class of therapeutic agent. Similarly, the biological binding domain can be designed to accommodate many types of therapeutics, including but not limited to monomethyl auristatin E (MMAE), calicheamicins (e.g., calicheamicin gamma1, enediyne esperamicin), maytansine (also referred to as maitansine), doxorubicin (also referred to as Adriamycin®, Myocet®, Rubex®; also known as hydroxydaunorubicin, hydroxydaunocycin), camptothecin and/or duocarmycins, including synthetic analogs adozelesin, bizelesin, and carzelesin; and any derivatives or analogues thereof.

Using the linker-free technology to join molecules for targeted drug delivery as described herein, chemotherapeutic agents currently used in the clinic to treat cancers, are also considered candidates for the development of novel bi-functional allosteric protein-drug molecules. Moreover, because binding domains can be added to a bi-functional allosteric protein or recombinant fusion protein comprising a scFv antibody that has a high binding affinity for a particular drug candidate, the number, for example, of 17-AAG molecules per scFv can be controlled by adding more ATP binding domains, for instance, at the C-terminus end of the scFv. The Protein Data Bank provides the information necessary for protein structural analysis, a key to finding a binding domain that can capture a particular ligand drug. With the completion of the Human Genome Project, DNA sequences encoding these binding domains have been identified and cDNAs that contain these DNA sequences are commercially available. In addition, protein crystallography and NMR-based protein structural analysis further assist in identifying which amino acids are involved in the actual interaction between the drug molecule and the binding pocket. Using the technology described herein, the number of potential chemotherapeutic agents that can be used in the development of novel bi-functional allosteric protein-drug molecules is significant. The tailored linker-free technology including biological binding domain selection, site-specific chemistry, and the introduction of functional groups to the drug can be optimized for each drug candidate.

The methods disclosed herein related to the process of producing the bi-functional allosteric protein-drug molecules as disclosed can be readily modified to produce a pharmaceutically acceptable salt of the bi-functional allosteric protein-drug molecules. Pharmaceutical compositions including such salts and methods of administering them are accordingly within the scope of the present disclosure.

Pharmaceutical Compositions

As disclosed herein, are pharmaceutical compositions, comprising the bi-functional allosteric protein-drug molecule and a pharmaceutical acceptable carrier described above. In some aspects, the therapeutic agent is an anti-cancer agent and the pharmaceutical composition is formulated for intravenous administration. The compositions of the present disclosure also contain a therapeutically effective amount of a bi-functional allosteric protein-drug molecule as described herein. The compositions can be formulated for administration by any of a variety of routes of administration, and can include one or more physiologically acceptable excipients, which can vary depending on the route of administration. As used herein, the term "excipient" means any compound or substance, including those that can also be referred to as "carriers" or "diluents." Preparing pharmaceutical and physiologically acceptable compositions is considered routine in the art, and thus, one of ordinary skill in the art can consult numerous authorities for guidance if needed.

The pharmaceutical compositions as disclosed herein can be prepared for oral or parenteral administration. Pharmaceutical compositions prepared for parenteral administration include those prepared for intravenous (or intra-arterial), intramuscular, subcutaneous, intraperitoneal, transmucosal (e.g., intranasal, intravaginal, or rectal), or transdermal (e.g., topical) administration. Aerosol inhalation can also be used to deliver the bi-functional allosteric protein-drug molecules. Thus, compositions can be prepared for parenteral administration that includes bi-functional allosteric protein-drug molecules dissolved or suspended in an acceptable carrier, including but not limited to an aqueous carrier, such as water, buffered water, saline, buffered saline (e.g., PBS), and the like. One or more of the excipients included can help approximate physiological conditions, such as pH adjusting and buffering agents, tonicity adjusting agents, wetting agents, detergents, and the like. Where the compositions include a solid component (as they may for oral administration), one or more of the excipients can act as a binder or filler (e.g., for the formulation of a tablet, a capsule, and the like). Where the compositions are formulated for application to the skin or to a mucosal surface, one or more of the excipients can be a solvent or emulsifier for the formulation of a cream, an ointment, and the like.

The pharmaceutical compositions can be sterile and sterilized by conventional sterilization techniques or sterile filtered. Aqueous solutions can be packaged for use as is, or lyophilized, the lyophilized preparation, which is encompassed by the present disclosure, can be combined with a sterile aqueous carrier prior to administration. The pH of the pharmaceutical compositions typically will be between 3 and 11 (e.g., between about 5 and 9) or between 6 and 8 (e.g., between about 7 and 8). The resulting compositions in solid form can be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

Methods of Treatment

Disclosed herein, are methods of treating a patient with cancer, the method comprising: (a) identifying a patient in need of treatment; and (b) administering to the patient a therapeutically effective amount of the pharmaceutical composition comprising bi-functional allosteric protein-drug molecules comprising a targeting moiety, one or more biological binding domains, and one or more therapeutic agents, wherein the therapeutic agent is allosterically bound to the biological binding domain, and a pharmaceutically acceptable carrier.

The pharmaceutical compositions described above can be formulated to include a therapeutically effective amount of a bi-functional allosteric protein-drug molecule. Therapeutic administration encompasses prophylactic applications. Based on genetic testing and other prognostic methods, a physician in consultation with their patient can choose a prophylactic administration where the patient has a clinically determined predisposition or increased susceptibility (in some cases, a greatly increased susceptibility) to a type of cancer.

The pharmaceutical compositions described herein can be administered to the subject (e.g., a human patient) in an amount sufficient to delay, reduce, or preferably prevent the onset of clinical disease. Accordingly, in some aspects, the patient is a human patient. In therapeutic applications, compositions are administered to a subject (e.g., a human patient) already with or diagnosed with cancer in an amount sufficient to at least partially improve a sign or symptom or to inhibit the progression of (and preferably arrest) the symptoms of the condition, its complications, and consequences. An amount adequate to accomplish this is defined as a "therapeutically effective amount." A therapeutically effective amount of a pharmaceutical composition can be an amount that achieves a cure, but that outcome is only one among several that can be achieved. As noted, a therapeutically effective amount includes amounts that provide a treatment in which the onset or progression of the cancer is delayed, hindered, or prevented, or the cancer or a symptom of the cancer is ameliorated. One or more of the symptoms can be less severe. Recovery can be accelerated in an individual who has been treated.

In some aspects, the cancer is a primary or secondary tumor. In other aspects, the primary or secondary tumor is within the patient's breast or lung. In yet other aspects, the cancer is associated with the expression of HER2 and/or the expression of an epidermal growth factor receptor.

Disclosed herein, are methods of treating a patient with cancer. The cancer can be any cancer. In some aspects, the cancer is breast cancer, ovarian cancer, lung cancer, or gastric cancer.

Amounts effective for this use can depend on the severity of the cancer and the weight and general state and health of the subject, but generally range from about 0.05 µg to about 1000 µg (e.g., 0.5-100 µg) of an equivalent amount of the bi-functional allosteric protein-drug molecule per dose per subject. Suitable regimes for initial administration and booster administrations are typified by an initial administration followed by repeated doses at one or more hourly, daily, weekly, or monthly intervals by a subsequent administration. For example, a subject can receive a bi-functional allosteric protein-drug molecule in the range of about 0.05 to 1,000 µg equivalent dose as compared to unbound or free therapeutic agent(s) per dose one or more times per week (e.g., 2, 3, 4, 5, 6, or 7 or more times per week). For example, a subject may receive 0.1 to 2,500 µg (e.g., 2,000, 1,500, 1,000, 500, 100, 10, 1, 0.5, or 0.1 µg) dose per week. A subject can also receive a bi-functional allosteric protein-drug molecule in the range of 0.1 to 3,000 µg per dose once every two or three weeks. A subject can also receive 2 mg/kg every week (with the weight calculated based on the weight of the bi-functional allosteric protein-drug molecule or any part or component of the bi-functional allosteric protein-drug molecule).

The total effective amount of a bi-functional allosteric protein-drug molecule in the pharmaceutical compositions disclosed herein can be administered to a mammal as a single dose, either as a bolus or by infusion over a relatively short period of time, or can be administered using a fractionated treatment protocol in which multiple doses are administered over a more prolonged period of time (e.g., a dose every 4-6, 8-12, 14-16, or 18-24 hours, or every 2-4 days, 1-2 weeks, or once a month). Alternatively, continuous intravenous infusions sufficient to maintain therapeutically effective concentrations in the blood are also within the scope of the present disclosure.

The therapeutically effective amount of one or more of the therapeutic agents present within the compositions described herein and used in the methods as disclosed herein applied to mammals (e.g., humans) can be determined by one of ordinary skill in the art with consideration of individual differences in age, weight, and other general conditions (as mentioned above). Because the bi-functional allosteric protein-drug molecules of the present disclosure can be stable in serum and the bloodstream and in some cases more specific, the dosage of the bi-functional allosteric protein-drug molecule including any individual component can be lower (or higher) than an effective dose of any of the individual components when unbound. Accordingly, in some aspects, the anti-cancer agent administered has increased efficacy or reduced side effects when administered as part of a bi-functional allosteric protein-drug molecule as compared to when the anti-cancer agent is administered alone or not as part of a bi-functional allosteric protein-drug molecule.

EXAMPLES

Example 1: Synthesis of the Bi-Functional Allosteric Protein-Drug Molecule

Figure 10:
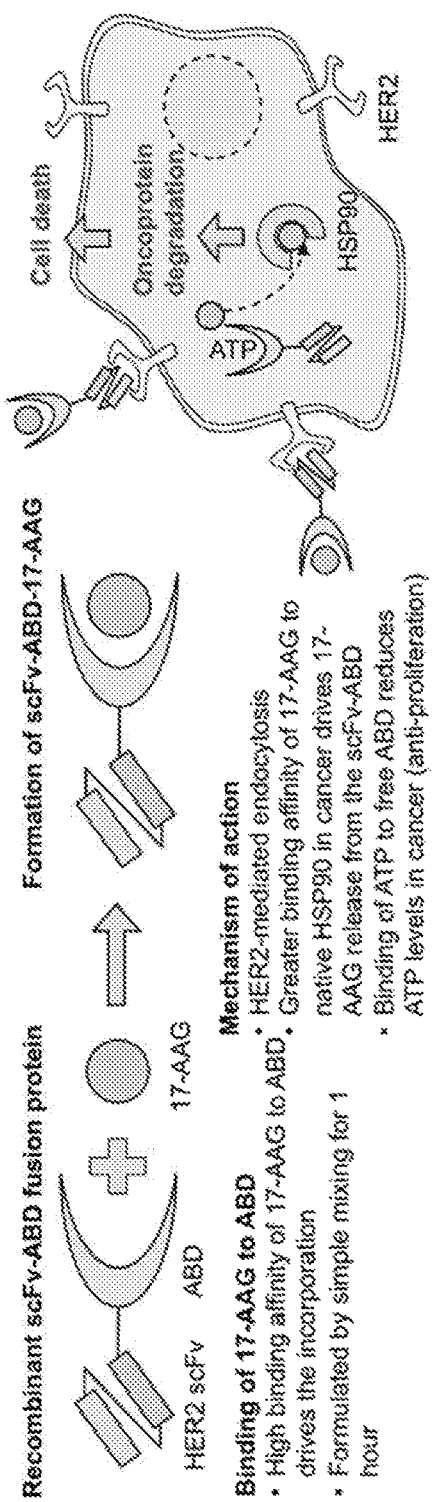
FIG. 10 illustrates a scheme showing the formation of the scFv-ATP binding domain (ABD)-17-AAG and the mechanism of action in HER2+ breast cancer.
Figure 11:
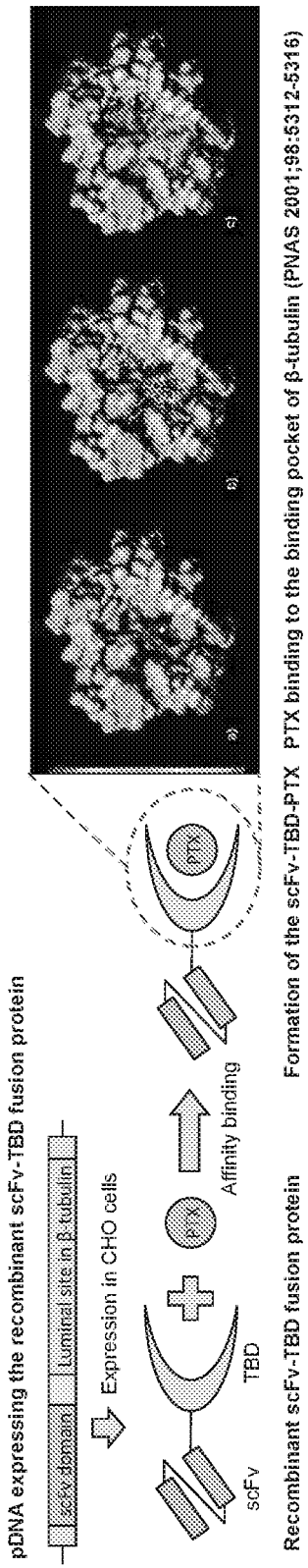
FIG. 11 illustrates a scheme showing the scFv-taxane-binding domain (TBD)-taxane molecule. A plasmid DNA encoding two protein domains: a HER2-scFv domain and the taxane-binding pocket of β-tubulin. Expression of this plasmid in CHO or HEK293 cells produces a recombinant fusion protein comprising the scFv domain and the taxane-binding domain. The high binding affinity of taxane to the luminal site drives the incorporation of PTX into the scFv-TBD fusion protein, which in turn leads to the formation of the scFv-TBD-PTX complex. In this formulation, the TBD not only solubilizes taxane in physiological buffers but also serves to prevent the exposure of taxane to aqueous environments. The shaded solvent accessible surface of the taxane-binding pocket of β-tubulin, colored according to degrees of hydrophobicity, appears on the right with the color key on the left (maximum, red; minimum, dark blue). The empty PTX-binding pocket (burnt orange) is highly hydrophobic (A). The binding center occupied by PTX, showing excellent shape complementarity (B). Surface recoloring illustrates the conversion of the hydrophobic cavity to a hydrophilic surface following the binding of PTX (C; Snyder J P et al. PNAS 2001; 98:5312-5316).

A scheme for constructing a bi-functional allosteric protein-drug molecule is shown in FIGS. 10 and 11. A recombinant fusion protein (e.g., bi-functional allosteric protein) comprising a protein transduction domain (PTD) and an ATP binding domain (ABD), (PTD-ABD), was used as a model to simulate the anti-cancer effects of 17-AAG delivered by the scFv-ABD because the PTD is capable of delivering cargo into cells. Geldanamycin (GM), an antibiotic that inhibits the function of HSP90, was used to develop a model bi-functional allosteric protein-drug molecule. The GM-binding domain of HSP90, located at the N-terminus of HSP90, contains the ATP binding pocket. The DNA fragment (0.7 kb) encoding the ATP binding domain was excised from the N-terminus of HSP90 (residues 9-232) and subcloned into the pET-28a expression vector. To prepare PTD-ABD fusion protein, a short DNA fragment encoding TAT was inserted at the N-terminus of the coding region for the ATP binding domain with a glycine spacer. The recombinant PTD-ABD was expressed in E. coli BL21 and purified by using fast protein liquid chromatography (FPLC) equipped with a $Ni^{2+}$-NTA column. The molecular weight of the final purified protein was determined by SDS-PAGE as shown in FIG. 1.

To confirm that the purified PTD-ABD fusion protein has a binding affinity for 17-AAG, a magnetic bead-based pull down assay was performed. GM was used instead of 17-AAG because biotin-17-AAG is not commercially available. Biotin-GM was mixed with the recombinant PTD-ABD fusion protein at 4° C. for 1 hour and streptavidin-magnetic beads were added to the mixture to pull down the bound protein. The PTD-ABD fusion protein was eluted from the beads (FIG. 1). A breast cancer cell lysate was added to the extracted sample (PTD-ABD+GM+beads) to verify that native HSP90 in the cancer cell lysate could replace the PTD-ABD that was already bound to GM+beads. In the PTD-ABD+GM beads+cell lysate group, the band of PTD-ABD became thinner compared to the PTD-ABD+GM beads group (FIG. 1, middle lane) and a new band representing native HSP90 (FIG. 1, right lane) was observed. These data show that the PTD-ABD can capture GM and that GM is released from the PTD-ABD spontaneously in the presence of native HSP90. This observation is explainable because, in a cancer cell, HSP90 has a higher binding affinity to GM than it has to the recombinant ATP binding domain. These results demonstrate that the ATP binding domain retains its binding affinity to GM when fused with another protein domain, confirming that the scFv-ATP binding domain will have the same binding affinity to 17-AAG.

Figure 2:
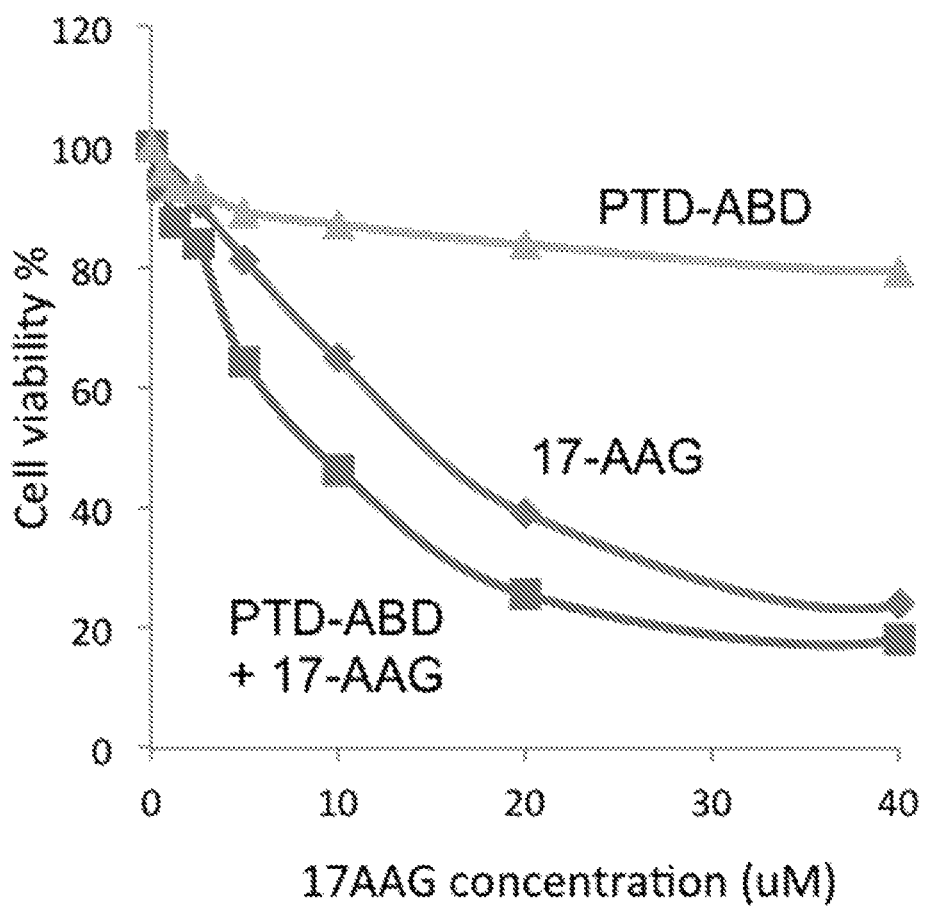
FIG. 2 shows the viability of MCF-7 breast cancer cells after delivery of either protein transduction domain-ATP binding domain (PTD)-ATP binding domain (ABD)-17-AAG, 17-AAG or PTD-ABD.

Example 2: Enhanced Anti-Cancer Efficacy of 17-AAG Delivered by the PTD-ABD Fusion Protein in Breast Cancer Cells To test the therapeutic efficacy of the formulation of PTD-ABD-17-AAG in MCF-7 breast cancer cells, the $IC_{50}$ value was determined in a dose-dependent manner. The $IC_{50}$ value is a measure of how effective a drug or therapeutic is and is defined as the concentration required to inhibit a biological process or component of a biological process (e.g., enzyme, cell, cell receptor) in half. The PTD-ABD-17-AAG was prepared as described above (Example 1) and administered to cancer cells. MCF-7 cells were exposed to one of the following formulations: 1) PTD-ABD-17-AAG; 2) 17-AAG; or 3) PTD-ABD. The $IC_{50}$ values were 10 µM and 15 µM for the PTD-ABD-17-AAG and 17-AAG treatment groups, respectively. These results show that delivery of 17-AAG by the PTD-ABD enhanced the anti-cancer efficacy of 17-AAG (FIG. 2). Further, the PTD-ABD fusion protein administered without 17-AAG resulted in a decrease in cell viability to 80%, confirming that the ATP binding domain also has anti-cancer efficacy/therapeutic properties.

Figures 3A, 3B:
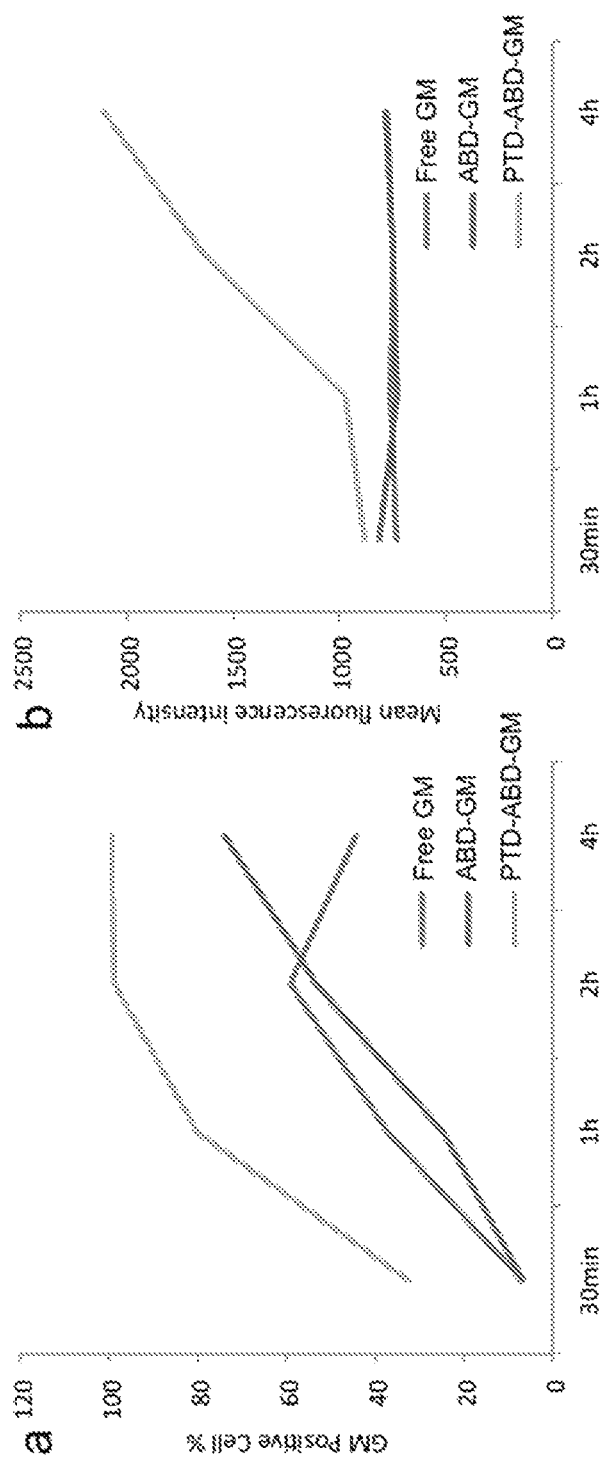
FIGS. 3A-B shows the uptake kinetics of geldanamycin into MCF-7 cells. Time kinetics of GM internalization (A), mean fluorescence intensity (MFI) values of the GM-positive cells (B), and kinetics of GM internalization (C), in a dose-dependent manner.
Figure 3C:
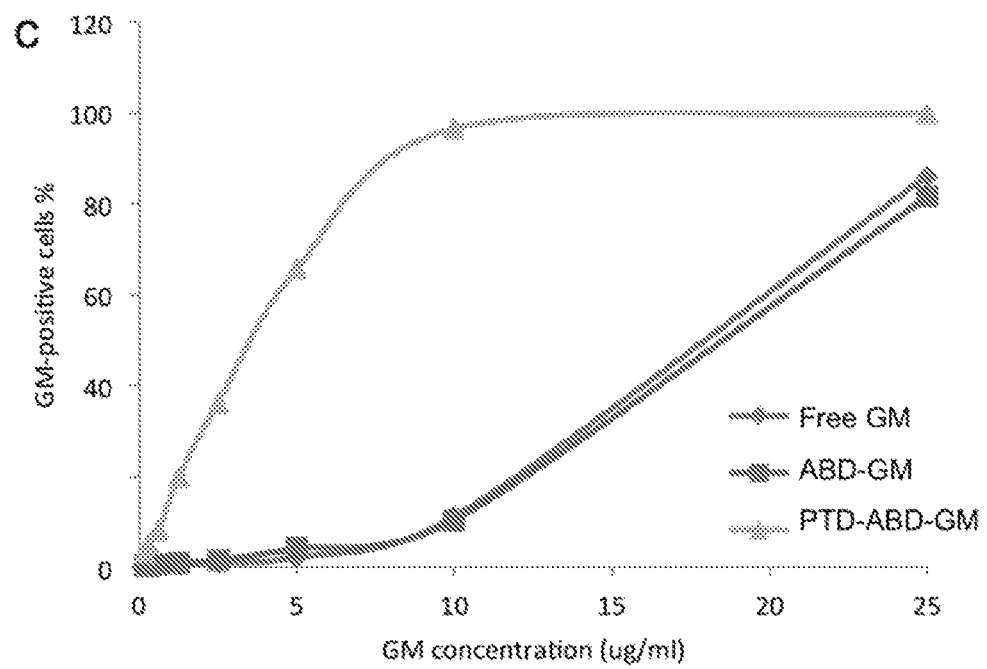

To test whether the PTD-ABD could improve the uptake kinetics of 17-AAG into cells, FITC-GM bound with the PTD-ABD or ABD alone was administered to MCF-7 cells in a time-dependent manner. At 2 hours post-treatment, the PTD-ABD internalized GM into 100% of the cell population, while 60% of the cell population was positive to FITC in the groups administered free GM and the ABD-GM (FIG. 3a). In addition, the mean fluorescence intensity (MFI), indicating the amount of GM internalized, increased continuously in a time-dependent manner in the PTD-ABD-GM group, whereas the free GM group and the ABD-GM group did not show this same pattern (FIG. 3b). Finally, 10 µg/ml of GM was sufficient to achieve internalization into 100% of the cell population when delivered by the PTD-ABD protein (FIG. 3c). On the other hand, both free GM and the ABD-GM did not achieve 100% cellular uptake even at a GM concentration of 25 µg/ml. These results indicate that the formation of the PTD-ABD-17-AAG improves the uptake kinetics of 17-AAG, reducing the effective dose of 17-AAG required to achieve anti-cancer efficacy.

Figure 4:
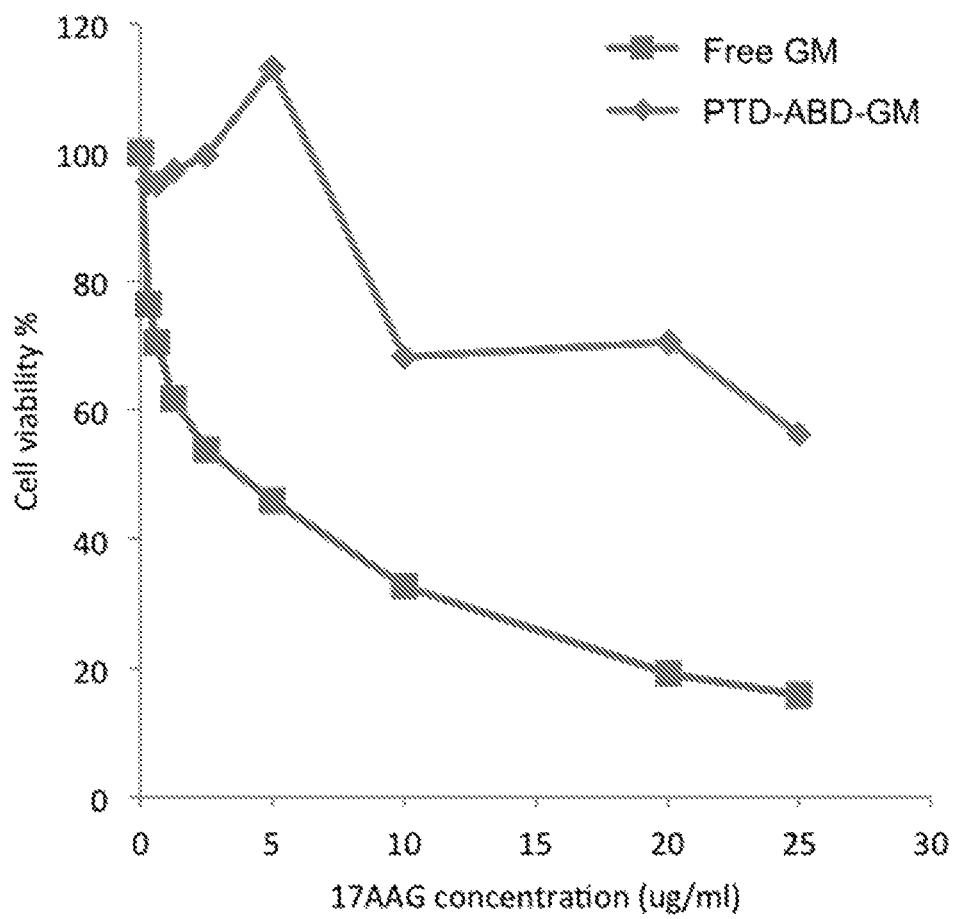
FIG. 4 is a graph demonstrating the effects of short-term treatment with PTD-ABD-17-AAG.

To examine whether the improved cellular uptake of 17-AAG by the PTD-ABD leads to enhanced efficacy of 17-AAG, breast cancer cells were exposed to 17-AAG or the PTD-ABD-17-AAG for 4 hours in a dose-dependent manner. The $IC_{50}$ value of the PTD-ABD-17-AAG was determined to be approximately 5 µg/ml, while that of free 17-AAG was approximately 25 µg/ml (FIG. 4). Due to the facilitated uptake of 17-AAG bound to the PTD-ABD, the short-term treatment of 17-AAG at low concentrations can increase the cellular concentration of 17-AAG, which results in the enhanced anti-cancer efficacy of 17-AAG. Free 17-AAG was not sufficiently internalized into cells during the short incubation time because of the poor uptake kinetics of free 17-AAG.

Figure 5:
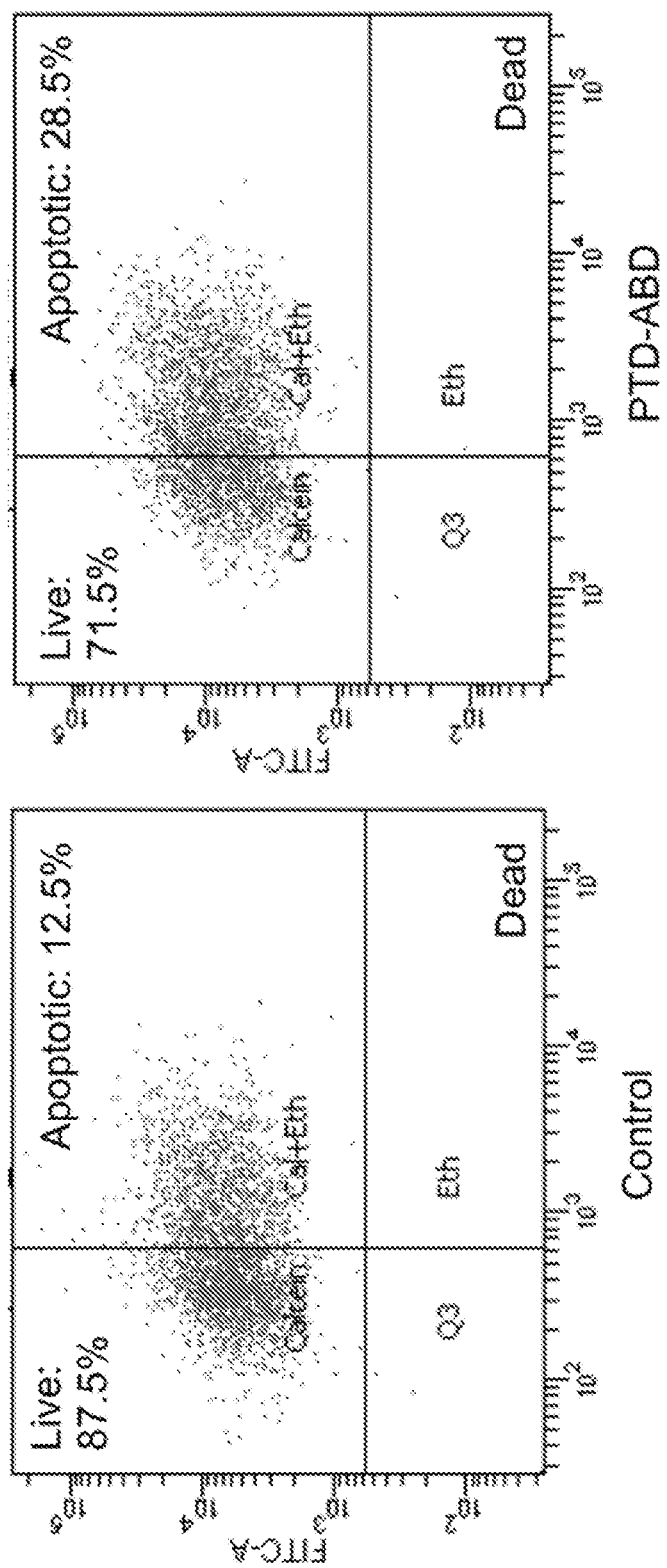
FIG. 5 shows the results of live/dead assay determined by fluorescence-activated cell sorting (FACS). Left: control; right: PTD-ABD.

To test whether the ATP binding domain is available to capture cellular ATP upon release of 17-AAG, thereby resulting in a reduction in the intracellular levels of ATP, an ATP assay (luciferase ATP detection kit; Invitrogen) was carried out. The ATP level in the PTD-ABD treatment group was decreased by 20% relative to control. This result indicates that the PTD-ABD fusion protein is capable of reducing cellular ATP levels and inhibiting cellular proliferation. Although the total number of viable cells was decreased to 80% compared to control (FIG. 2), it is unknown whether the decreased cell viability was due to cell death or to an inhibition of cellular proliferation caused by the reduced levels of intracellular ATP. To this end, a live/dead assay was performed, which verified an increase in the apoptotic cell population in the PTD-ABD group, meaning that the decreased cell viability was due to the increased cellular apoptosis (FIG. 5). Consequently, the intracellular deposit of PTD-ABD leads to a decrease in cellular ATP, which in turn induces apoptosis and cell death. This observation provides evidence that the PTD-ABD can reduce intracellular levels of ATP and induce apoptosis.

Through the above experiments, the following findings have been confirmed: 1) an ATP binding domain with a high binding affinity to 17-AAG can be produced; 2) the PTD-ABD, as a model system, is capable of delivering 17-AAG into cells; 3) PTD-ABD-17-AAG improves the uptake kinetics of 17-AAG; 4) the improved cellular uptake of 17-AAG leads to enhanced anti-cancer efficacy of 17-AAG; 5) the ATP binding domain can reduce intracellular levels of ATP; and 6) the reduced intracellular levels of ATP induces apoptosis. In addition, the ATP binding domain when fused with another protein domain retains its binding affinity to 17-AAG, demonstrating that the scFv-ABD likely retains the dual functionalities of targeting HER2 and binding 17-AAG in the formation of a bi-functional allosteric protein.

Example 3: Stability of ABD-GM in Serum

Figure 6:
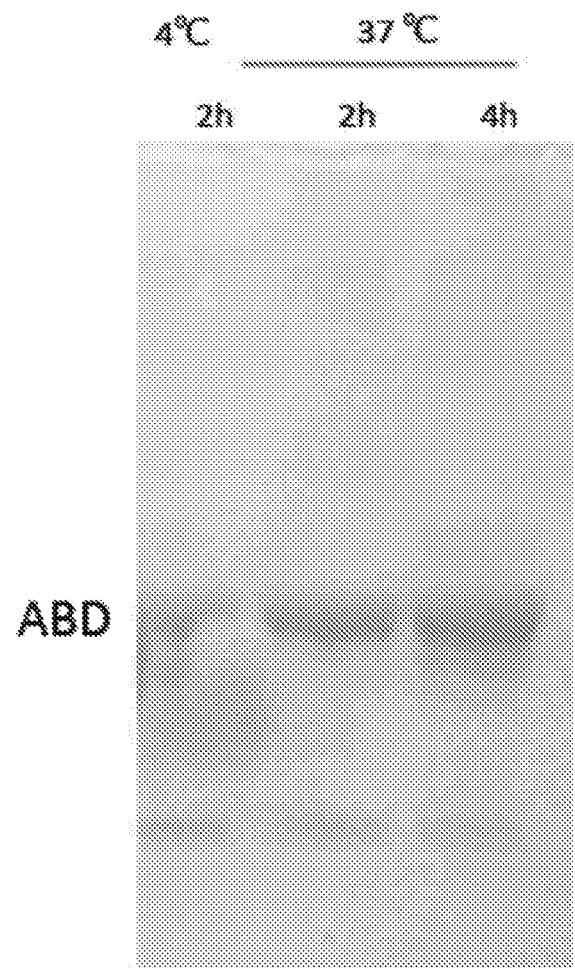
FIG. 6 is a picture of an SDS-PAGE showing the control and ABD-geldanamycin (ATP binding domain-GM) (lane 1), the ABD-GM incubated in the presence of serum for 2 hours at 37° C. (lane 2) and the ABD-GM incubated in the presence of serum for 4 hours at 37° C. (lane 3).

To determine the stability of ABD-GM in serum, the ATP-binding domain (ABD) was first incubated with GM-biotin to form ABD-GM. Next, ABD-GM was mixed with serum at the final serum concentration of 67% followed by incubation at 37° C. The bound protein was isolated by streptavidin-magnetic beads and eluted for SDS-PAGE. The results show that the ABD bands remained the same size as control and ABD-GM remained bound in the presence of serum for 4 hours of incubation at 37° C. (FIG. 6). ABD-GM did not dissociate, nor did the GM bind to other proteins in the serum, as no other bands were observed. These data indicate that ABD-GM is stable in serum for an extended period of time.

Figures 7A, 7B:
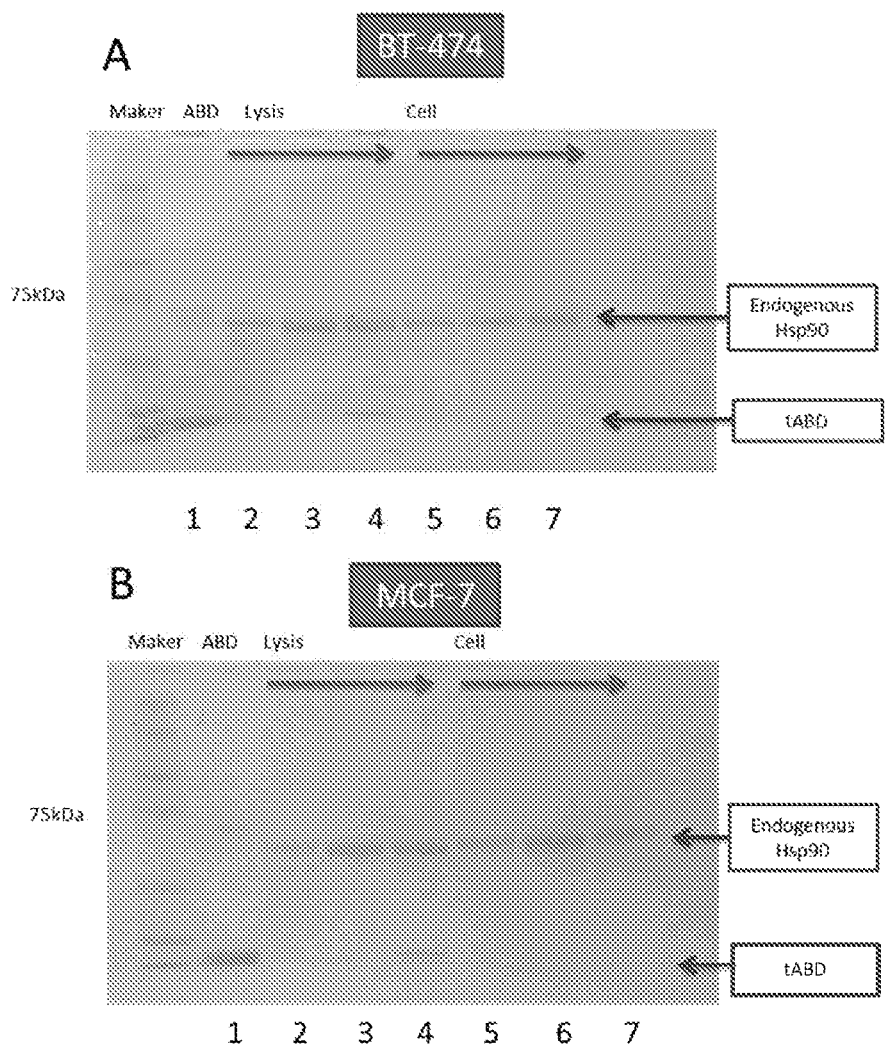
FIGS. 7A-B illustrates the dissociation of biotin-geldanamycin (BGM) in BT-474 (A) and MCF-7 (B) cancer cell lines.
Figures 8A, 8B:
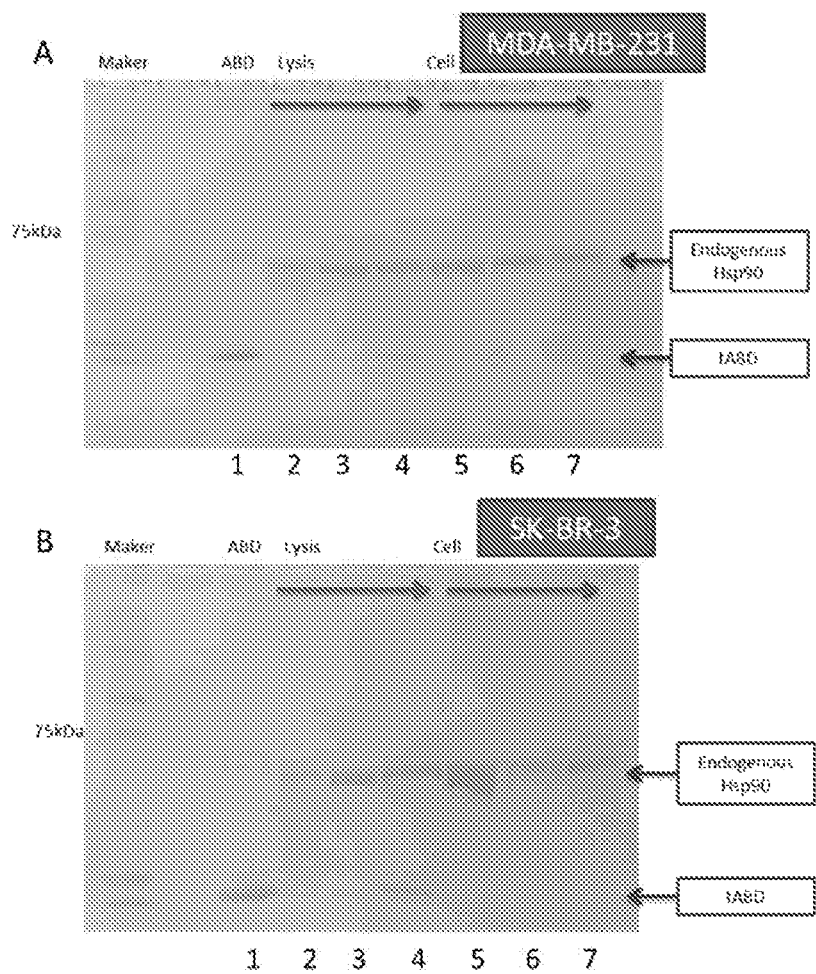
FIGS. 8A-B illustrates the dissociation of biotin-geldanamycin (BGM) in MDA-MB-231 (A) and SK-BR-3 (B) cancer cell lines.

Example 4: Determination of the Dissociation Kinetics of GM from the scFv-ABD in Breast Cancer Cells The ability of GM to be released from the PTD-ATP-binding domain and then bind to native HSP90 in cancer cells was studied using recombinant PTD-ABD protein and cancer cell lysate. Four different breast cancer cell lines were used: two cell lines that over express HER2, BT-474 (FIG. 7A) and SK-BR-3 (FIG. 8B); and two normal cell lines, MCF-7 (FIG. 7B) and MDA-MB-231 (FIG. 8A; 2×10⁵ cells/well). As described in Example 1, the PTD-ABD fusion protein was prepared as follows, a short DNA fragment encoding TAT (100 µg) was inserted at the N-terminus of the coding region for the ATP binding domain with a glycine spacer (FIG. 7, 8, lane 1). Cancer cell lysate (FIG. 7, lane 2) was also incubated with GM-biotin (FIG. 7, 8, lane 3). The results show that the bound protein to GM is native HSP90 (MW=~70 kDa) and that GM specifically binds to HSP90 in a cancer cell.

Then, a mixture of cancer cell lysate and ABD was incubated with biotin-GM (FIG. 7, 8, lane 4) at 4° C. for 1 hour showing that the primary binding protein for GM is HSP90 because a very thick HSP90 band is observed, while a thin and weak ABD band is detected. Next, the cancer cells were incubated with ABD, then, lysed, and the cell lysate was incubated with biotin-GM (FIG. 7, 8, lane 5). The results show that GM mostly binds to native HSP90. Cancer cells were then incubated with ABD-GM for 2 hours (FIG. 7, 8, lane 6) or 4 hours (FIG. 7, 8, lane 7) and then lysed. ABD was not detected, while native HSP90 was observed to be the bound protein to GM. These results indicate that GM bound to ABD in fact internalized into cells and was subsequently released from ABD and migrated to bind to native HSP90.

Taken together, the results show that ABD-GM dissociates to release GM, which in turn binds to native HSP90 in cancer cells. The mechanism of this dissociation is likely due to the fact that GM has a weak binding affinity to recombinant ABD (micromolar affinity) compared to native HSP90 (nanomolar affinity).

Example 5: Construction of a Recombinant HER2-scFv-ABD Fusion Protein

A series of experiments were carried out to confirm the binding between HER2-ABD and biotin-GM. First, antibody activity was examined in comparison with HER monoclonal Ab (mAb). The results show that about 40% of the cell population was HER2 positive in SK-BR-3 cells using HER mAb alone and about 10% of the cell population was HER2 positive in SK-BR-3 with exposure to HER2-scFv-ABD, whereas only 1% of the cell population was positive in MDA-MB-231, a HER-2 normal breast cancer cell line. Although these data suggest that an increased amount of the HER2-scFv-ABD fusion protein is needed to detect an increased number of HER2-positive cells, the results show that the HER2-scFv-ABD does in fact, retain the HER2 antibody activity.

Figures 9A, 9B:
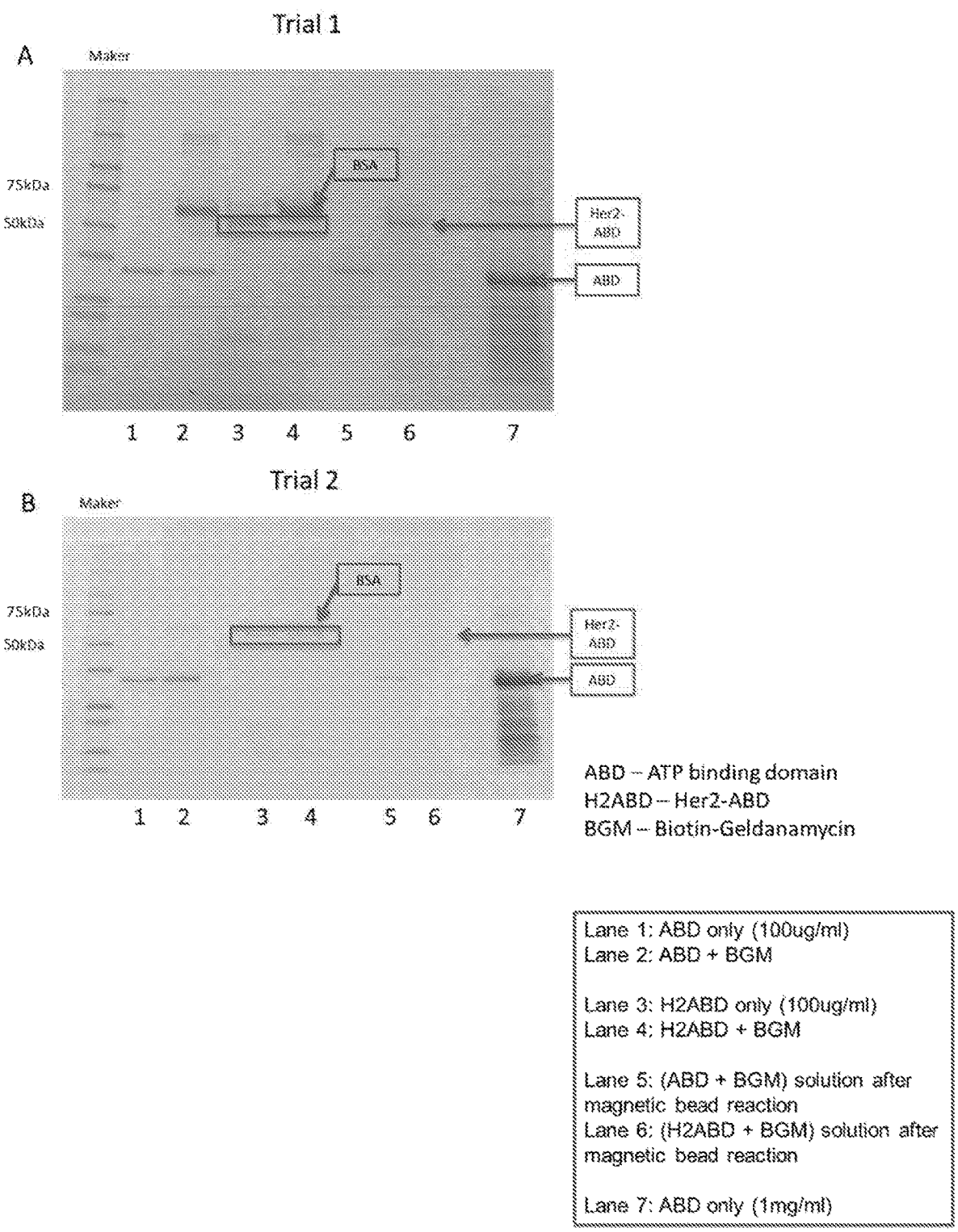
FIGS. 9A-B are pictures depicting the binding of geldanamycin (GM) to the HER2 scFv-ABD fusion protein in trial 1 (A) and trial 2 (B).

The function of the ABD in the HER2-scFv-ABD was examined through a GM binding assay (FIG. 9; two trials (A, B)). Lane 4 shows the binding of the HER2-scFv-ABD to GM while lane 3 shows the HER2-scFv-ABD protein. A clear band appeared in lane 4 at the same location as lane 3, indicating that the bound protein to GM is the HER2-scFv-ABD fusion protein. All of the other groups served as controls. These results confirm that the HER2-scFv-ABD binds to GM. Taken together, these observations indicate that the HER2-scFv-ABD is bi-functional because it binds to the HER2 antibody while ABD captures 17-AAG.

Example 6: Synthesis of the scFv-TBD-Taxane Molecule

A scheme for constructing a bi-functional allosteric protein-drug molecule comprising a single-chain fragment (scFv) antibody as a targeting moiety and a 0-tubulin luminal site domain, referred to as a taxane-binding domain (TBD) to incorporate paclitaxel (PTX), a microtubule-stabilizing agent is shown in FIG. 11. An important component in producing scFv-TBD-taxane is the TBD. The TBD permits stable transport of taxane in the bloodstream and can release taxane (e.g., PTX) in the presence of microtubules within the target cells. With Abraxane (paclitaxel protein-bound particles), the hydrophobic pockets of human serum albumin (HSA) bind a wide range of endogenous and exogenous compounds to adsorb and solubilize PTX. The overall PTX-HSA binding affinity is calculated as K=1.43×$10^4 M^{-1}$ and continuous binding studies have identified two binding sites in HSA, one with a high binging affinity of $K_a$=2.4×$10^6$ $M^{-1}$ and the other with an intermediate binding affinity of K=1.0×$10^5$ $M^{-1}$. The binding affinity of PTX to microtubules is approximately $K_a$=6.0×$10^7$ $M^{-1}$. This difference in the binding affinities of PTX to HSA versus microtubules provides the mechanism for the release of PTX from HSA in cancer cells. These differences in binding affinities serve as the basis for a site-directed mutagenesis approach, i.e., to increase the affinity of PTX to the taxane-binding domain so that it is high enough to provide stability in the circulation such that it is superior to HSA, but low enough to facilitate release of PTX to reach the microtubules within the target cancer cells.

Example 7: Construction of a Recombinant HER2-scFv-ABD Bi-Functional Allosteric Protein Capturing Multiple Therapeutic Molecules A set of experiments were carried out to confirm that the bi-functional allosteric protein-drug molecule can accommodate one or more biological binding domains (e.g., ABDs), and thus carry a greater number of (one or more) therapeutic agents (e.g., 17-AAG) than a bi-functional allosteric protein-drug molecule comprising a single (e.g., one) biological binding domain (e.g., ABD). For this, the DNA fragment encoding the ABD located at the N-terminus of HSP90 was excised from the N-terminus of HSP90 (residues 9-232) and sub-cloned into the HER2-scFv expression vector with a non-flexible hinge. To develop a bi-functional allosteric protein-drug molecule comprising three ABDs, three ABDs were connected by a linker, GGGS, and then the full sequence containing the three ABDs and two linkers was inserted into the expression vector. This expression vector was transfected into HEK293 cells by using a commercially available transfection kit.

The cells were cultured for 3 days and the culture media was collected to purify the recombinant bi-functional allosteric protein-drug molecule. These bi-functional allosteric protein-drug molecules were purified using a FPLC equipped with Protein L column. The purified bi-functional allosteric protein-drug molecule were dialyzed, concentrated, and kept frozen until use. The bi-functional allosteric protein-drug molecule was verified by SDS-PAGE and western blot (anti-His tag antibody) as shown in FIG. 12. Binding of the bi-functional allosteric protein-drug molecule with GM was confirmed by a magnetic bead-based pull down assay. Each of the bi-functional allosteric protein-drug molecules was mixed with biotin-GM and incubated for 30 minutes at 4° C. After the incubation, the biotin-GM was captured by using streptavidin-magnetic beads. The protein bound to the biotin-GM was eluted by heating in the presence of SDS. The eluted sample was electrophoresed on a SDS-PAGE gel. Western blot was conducted following the SDS-PAGE in order to confirm the specific binding of the recombinant proteins to GM.

Figures 12A, 12B:
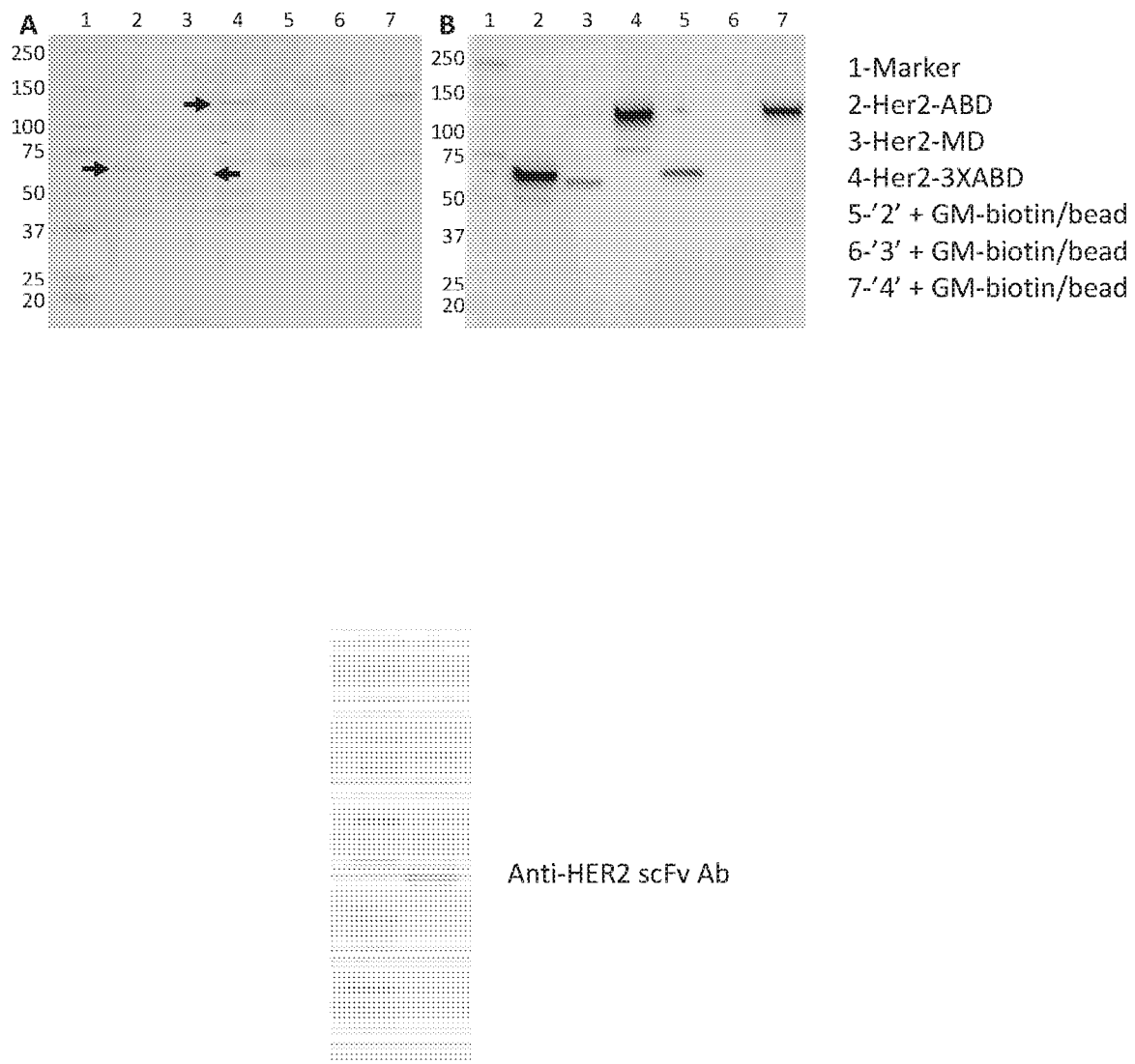
FIG. 12A-B shows SDS-PAGE (A) and Western blot (B) of the proteins and the proteins bound to GM-biotin. Lane 1: Protein marker; Lanes 2-4: Purified proteins; Lanes 5-7: GM-bound proteins; Lanes 2 and 5: HER2 scFv-ABD; Lanes 3 and 6: HER2 scFv-MD; Lanes 4 and 7: the HER2 scFv-ABD x 3. Arrows indicate the location of the proteins.

The results show that both the HER2 scFv-ABD and the HER2 scFv-ABD-ABD-ABD can capture 17-AAG, whereas the HER2 scFv-MD (middle domain; control) has no affinity for 17-AAG (See FIG. 12A, lanes 5-7). These data verify that the biological affinity of 17-AAG to ABD is specific.

Example 8: Determine the Internalization of Geldanamycin

To verify that the TAT-ABD facilitates the internalization of geldanamycin (GA) into cells, dual fluorescence-based detection was used. The TAT-ABD protein was labeled with Rhodamine, mixed with FITC-GA, incubated for 30 minutes at 4° C., and then contacted with one of the following cell lines; BT-474 (HER2+), SKBR-3 (HER2+), MDA-MB-231 (HER2−), and MCF-7 (HER2−). Free-FITC-GA-treated, non-treated, or rhodamine-TAT-ABD-treated cells were prepared as control groups. After 4 hours, the cells were washed and harvested for FACS analysis. FACSCanto II was used to analyze the cells. The results are as follows.

Figures 13A, 13B:
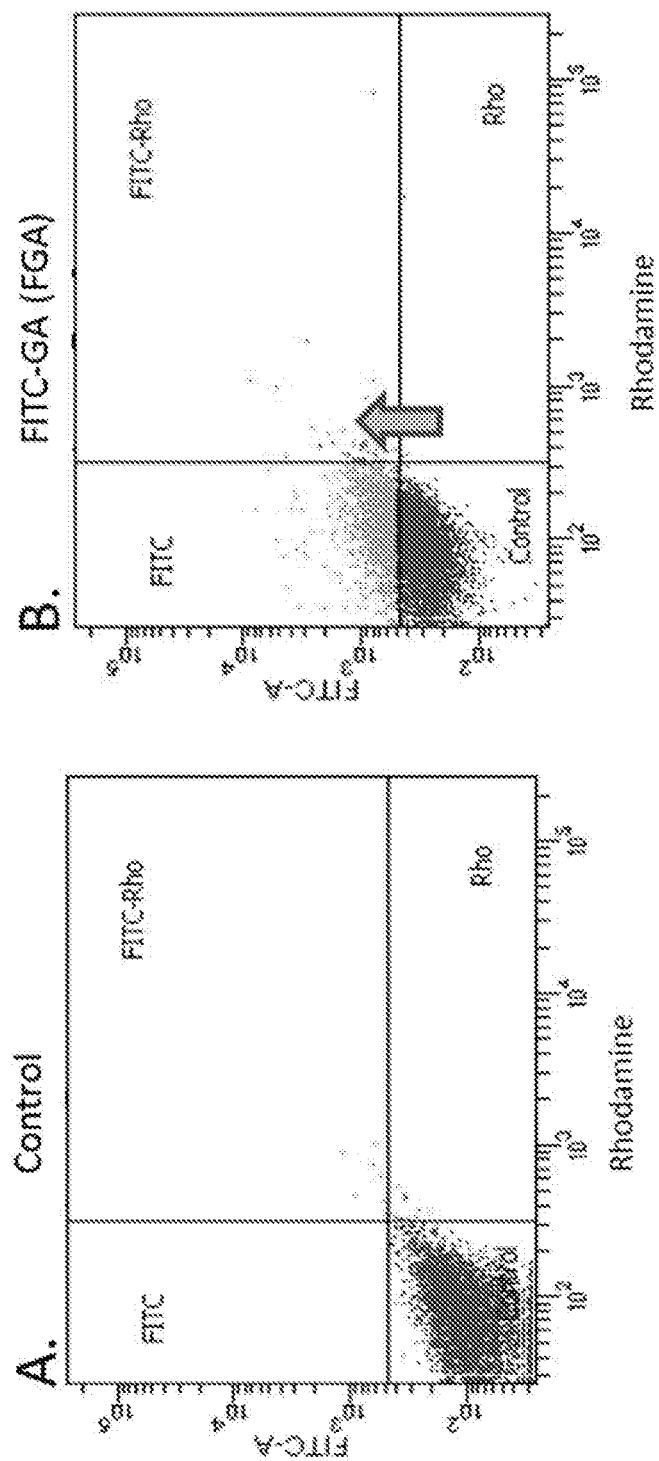
FIG. 13A-E shows that TAT-ABD facilitates the internalization of geldanamycin (GA) into BT-474 cells. A. Control, non-treated cells. B. FITC-GA, FITC-labeled GA internalized into the cells. C. Rhodamine-TAT-ABD, Rhodamine-labeled TAT-ABD without GA resulting in the internalization of the TAT-ABD protein into the cells. D. Rhodamine-TAT-ABD+FITC-GA, combination of B. plus C., resulting in the internalization of both TAT-ABD and GA into the cells. E. A bar graph showing the percent intracellular uptake of A.-D.
Figures 13C, 13D:
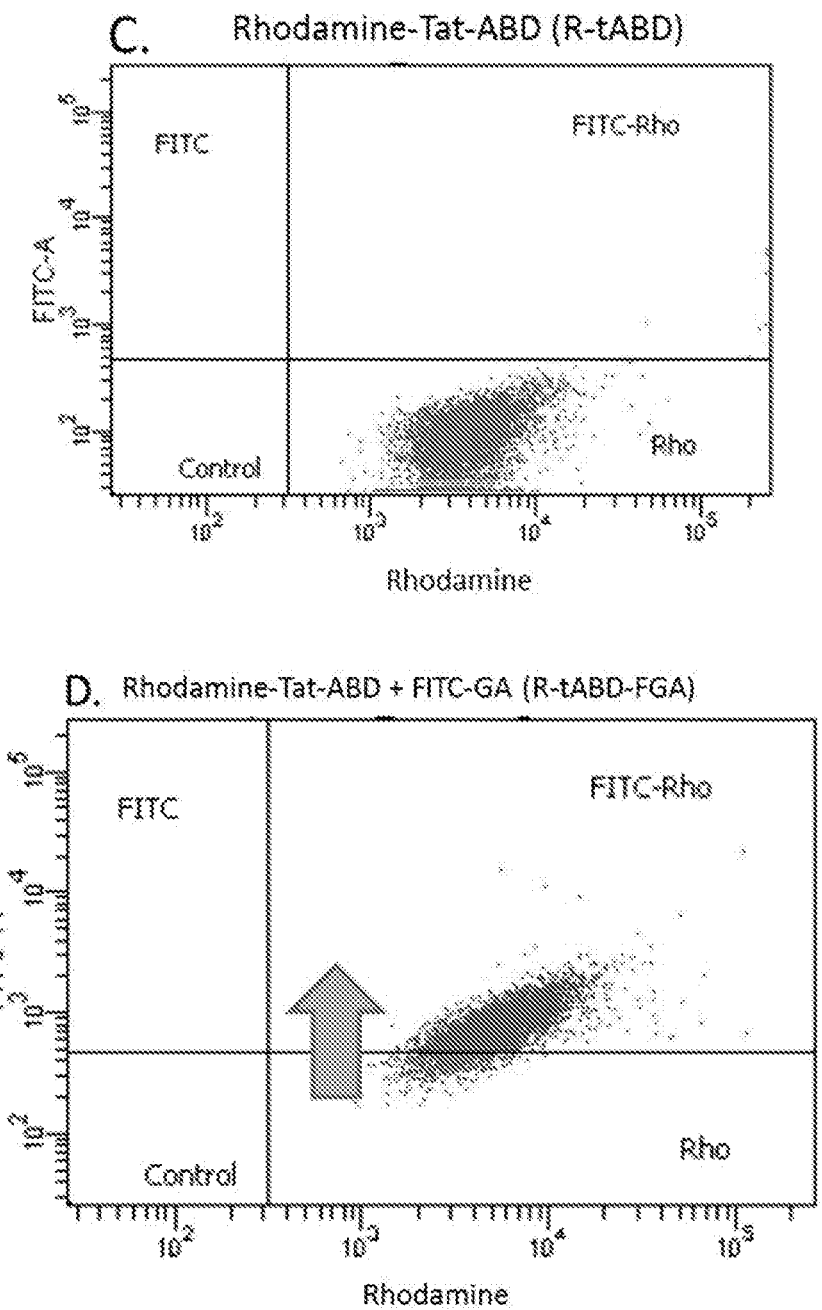
Figure 13E:
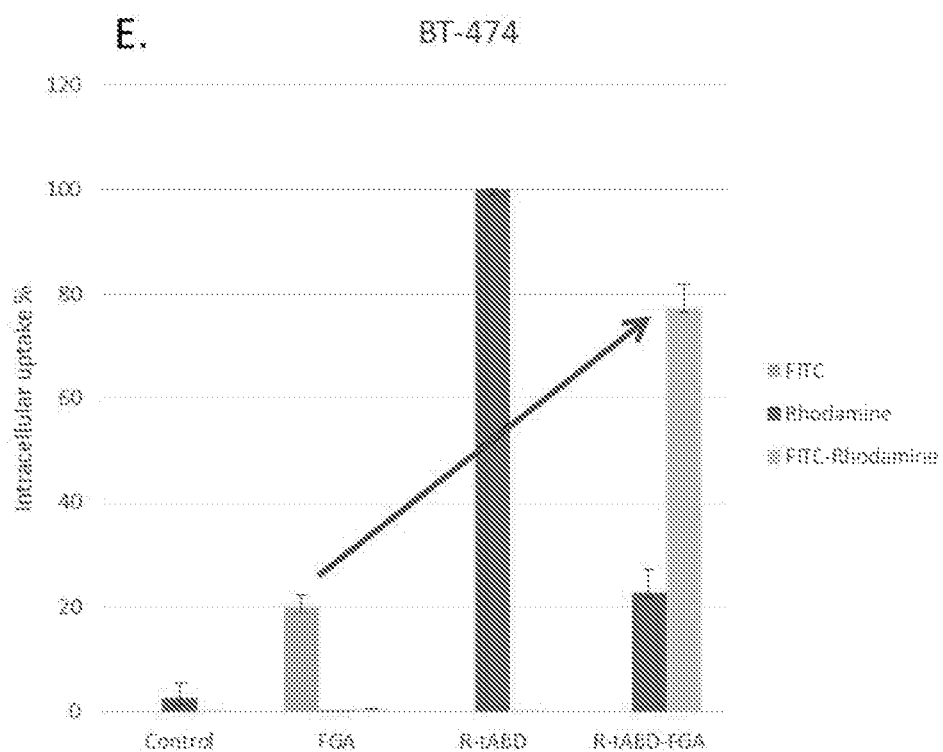
Figures 14A, 14B:
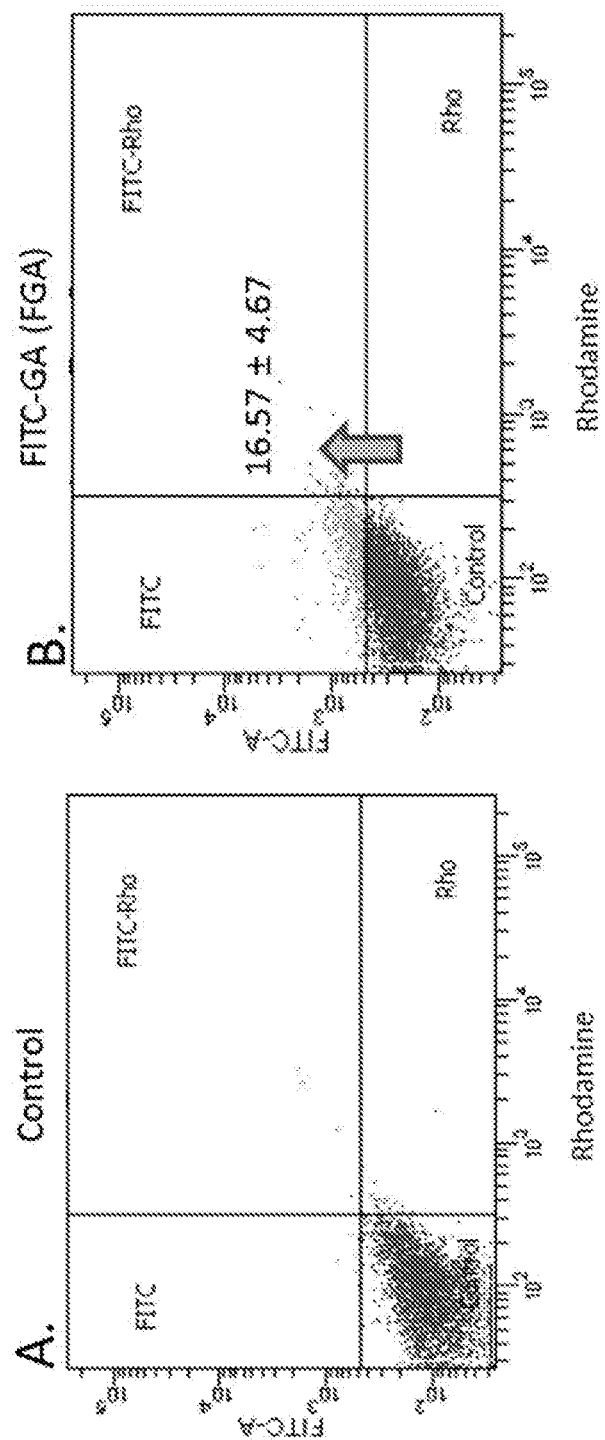
FIG. 14A-E shows that TAT-ABD facilitates the internalization of geldanamycin (GA) into MCF-7 cells. A. Control, non-treated cells. B. FITC-GA, FITC-labeled GA internalized into the cells. C. Rhodamine-TAT-ABD, Rhodamine-labeled TAT-ABD without GA resulting in the internalization of the TAT-ABD protein into the cells. D. Rhodamine-TAT-ABD+FITC-GA, combination of B. plus C., resulting in the internalization of both TAT-ABD and GA into the cells. E. A bar graph showing the percent intracellular uptake of A.-D.
Figure 14C:
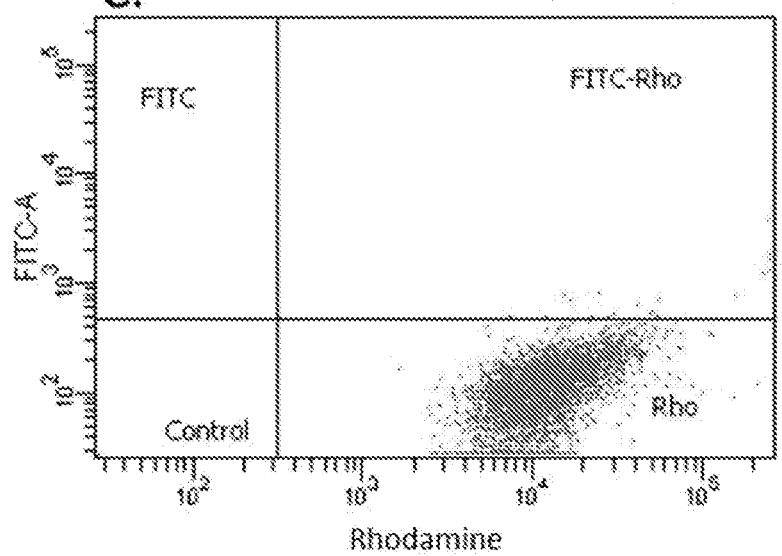
Figure 14D:
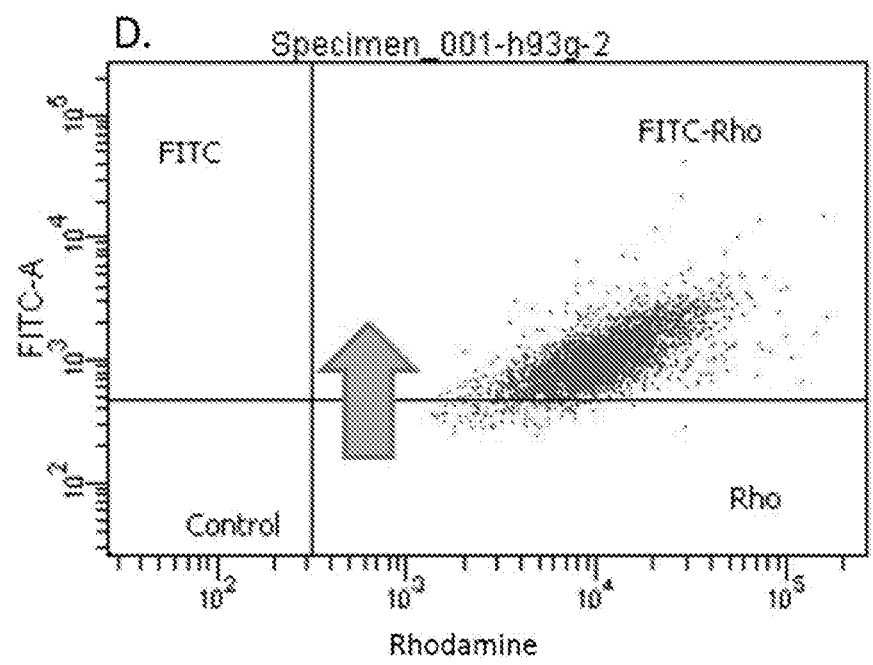
Figure 14E:
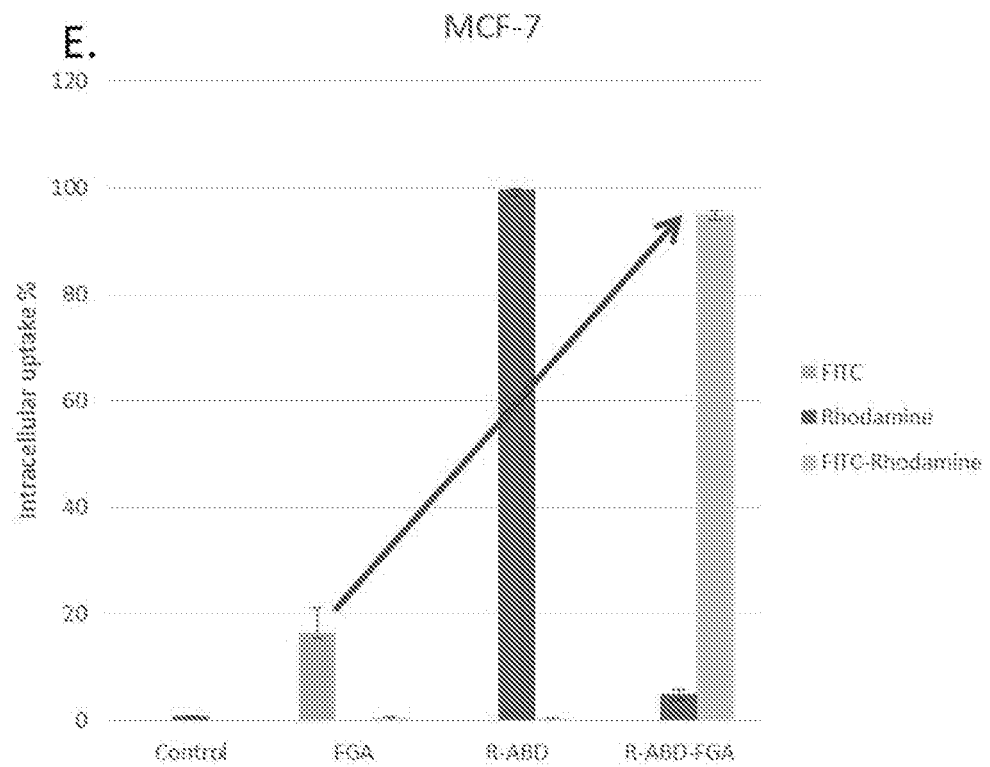
Figures 15A, 15B:
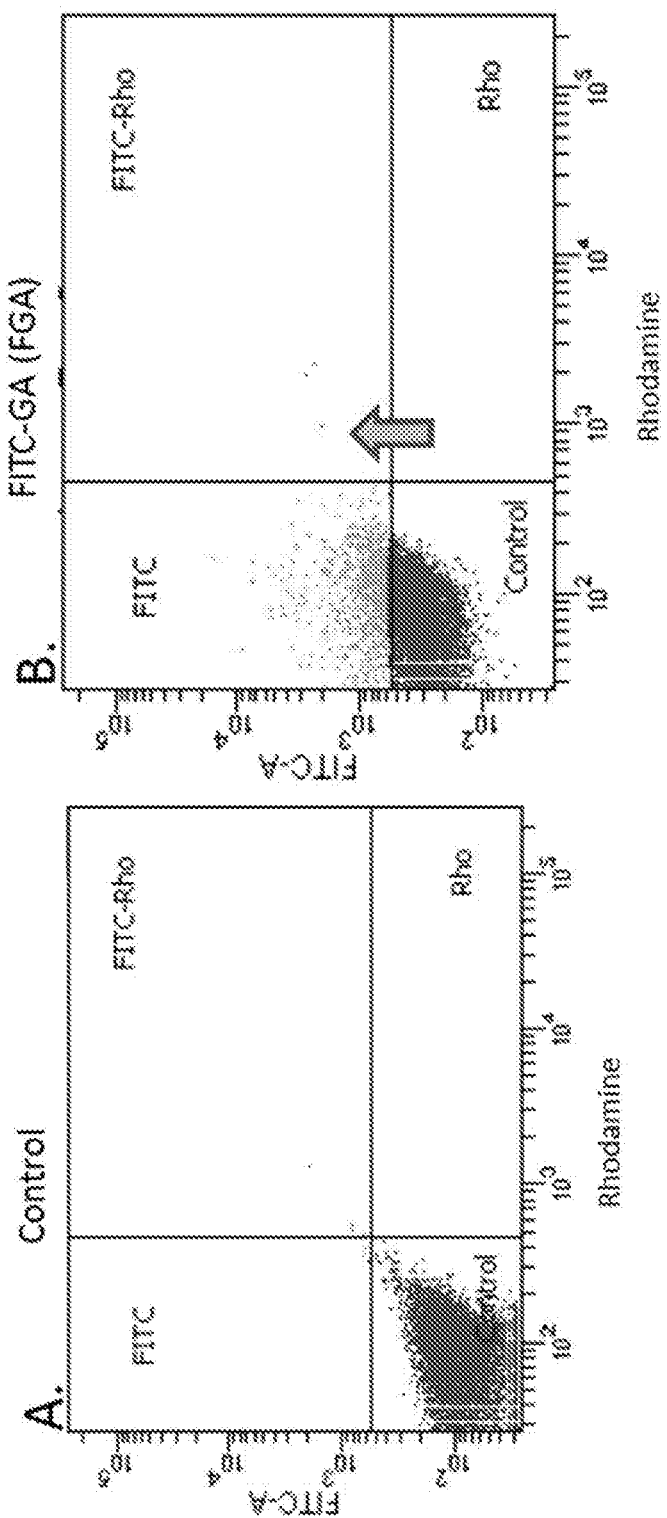
FIG. 15A-E shows that TAT-ABD facilitates the internalization of geldanamycin (GA) into MCF-7 cells. A. Control, non-treated cells. B. FITC-GA, FITC-labeled GA internalized into the cells. C. Rhodamine-TAT-ABD, Rhodamine-labeled TAT-ABD without GA resulting in the internalization of the TAT-ABD protein into the cells. D. Rhodamine-TAT-ABD+FITC-GA, combination of B. plus C., resulting in the internalization of both TAT-ABD and GA into the cells. E. A bar graph showing the percent intracellular uptake of A.-D.
Figure 15C:
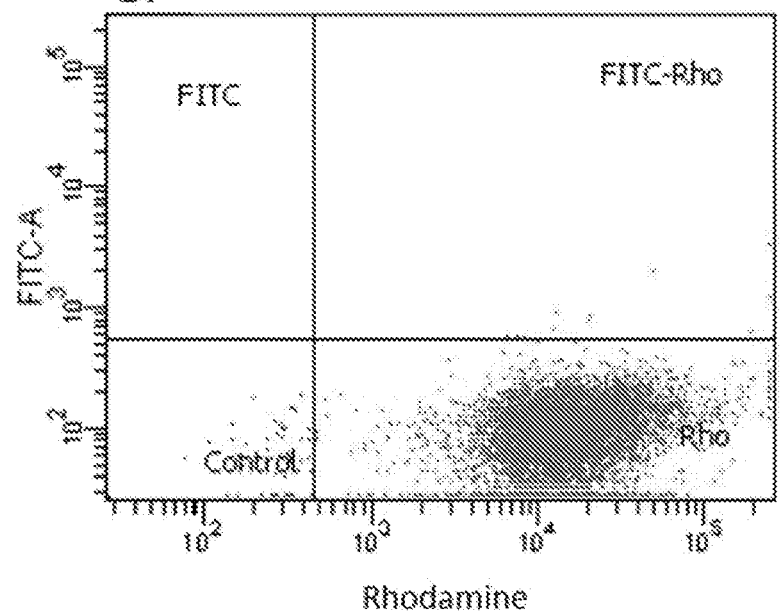
Figure 15D:
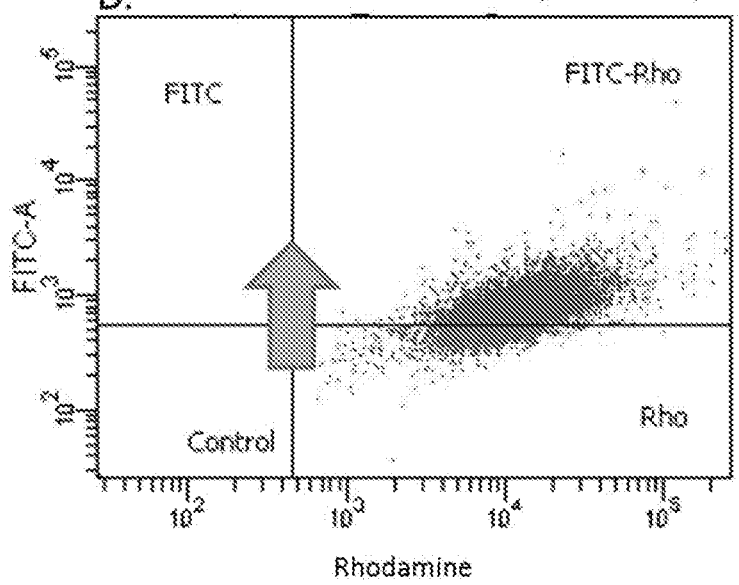
Figure 15E:
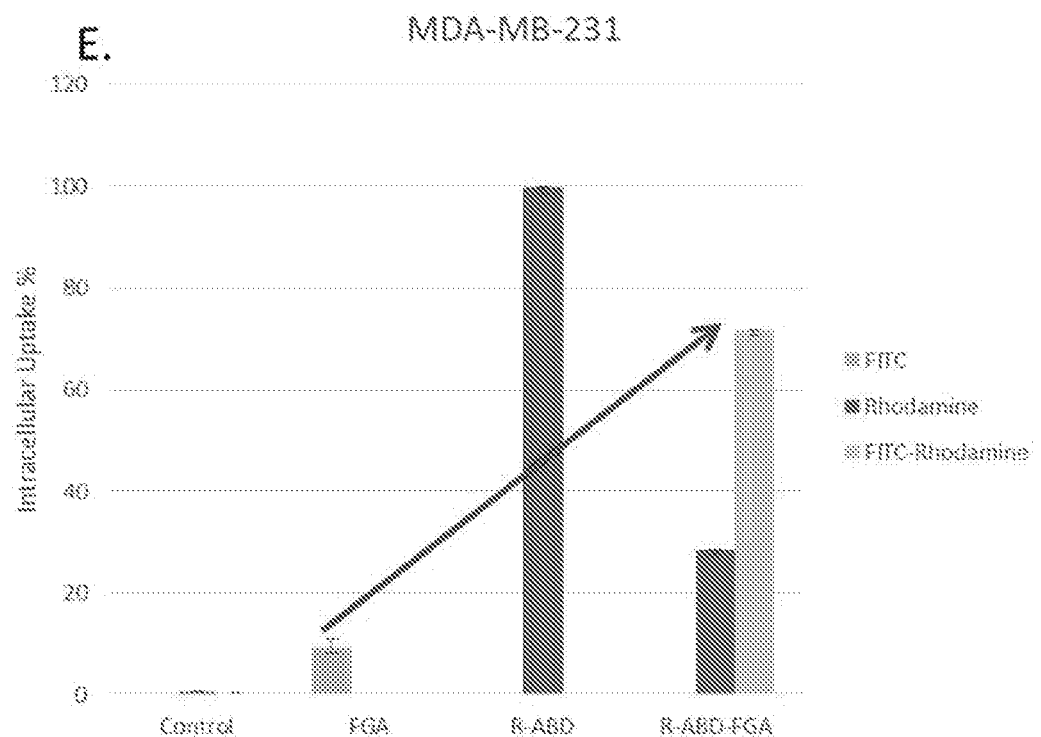

BT-474 cell line: Intracellular uptake of FITC-GA was approximately 20% without the TAT-ABD protein (FIG. 13; green bar). TAT-ABD internalized into 100% of the cells (FIG. 13; R-tABD). TAT-ABD plus FITC-GA internalized into approximately 70% of the cells (FIG. 13; R-tABD-FGA). Approximately 25% the cells were positive to solely Rhodamine.

MCF-7 cell line: Intracellular uptake of FITC-GA was approximately 15% without the TAT-ABD protein (FIG. 14; FGA). TAT-ABD internalized into 100% of the cells (FIG. 14; R-tABD). TAT-ABD plus FITC-GA internalized into approximately 95% of the cells (FIG. 14; R-tABD-FGA). Approximately 5% cells were positive to solely Rhodamine.

MDA-MB-231 cell line: Intracellular uptake of FITC-GA was approximately 10% without the TAT-ABD protein (FIG. 15; FGA). TAT-ABD internalized into 100% of the cells (FIG. 15; R-tABD). TAT-ABD plus FITC-GA internalized into approximately 70% of the cells (FIG. 15; R-tABD-FGA). Approximately 30% cells were positive to solely Rhodamine.

Figures 16A, 16B:
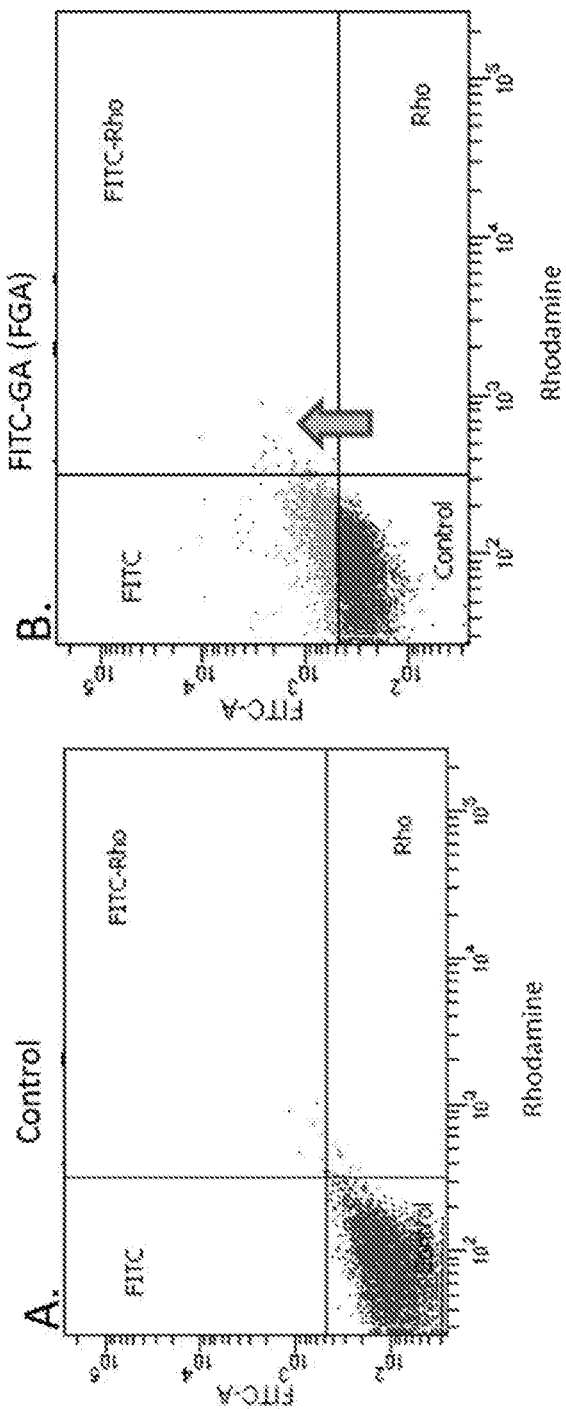
FIG. 16A-E shows that TAT-ABD facilitates the internalization of geldanamycin (GA) into MCF-7 cells. A. Control, non-treated cells. B. FITC-GA, FITC-labeled GA internalized into the cells. C. Rhodamine-TAT-ABD, Rhodamine-labeled TAT-ABD without GA resulting in the internalization of the TAT-ABD protein into the cells. D. Rhodamine-TAT-ABD+FITC-GA, combination of B. plus C., resulting in the internalization of both TAT-ABD and GA into the cells. E. A bar graph showing the percent intracellular uptake of A.-D.
Figures 16C, 16D:
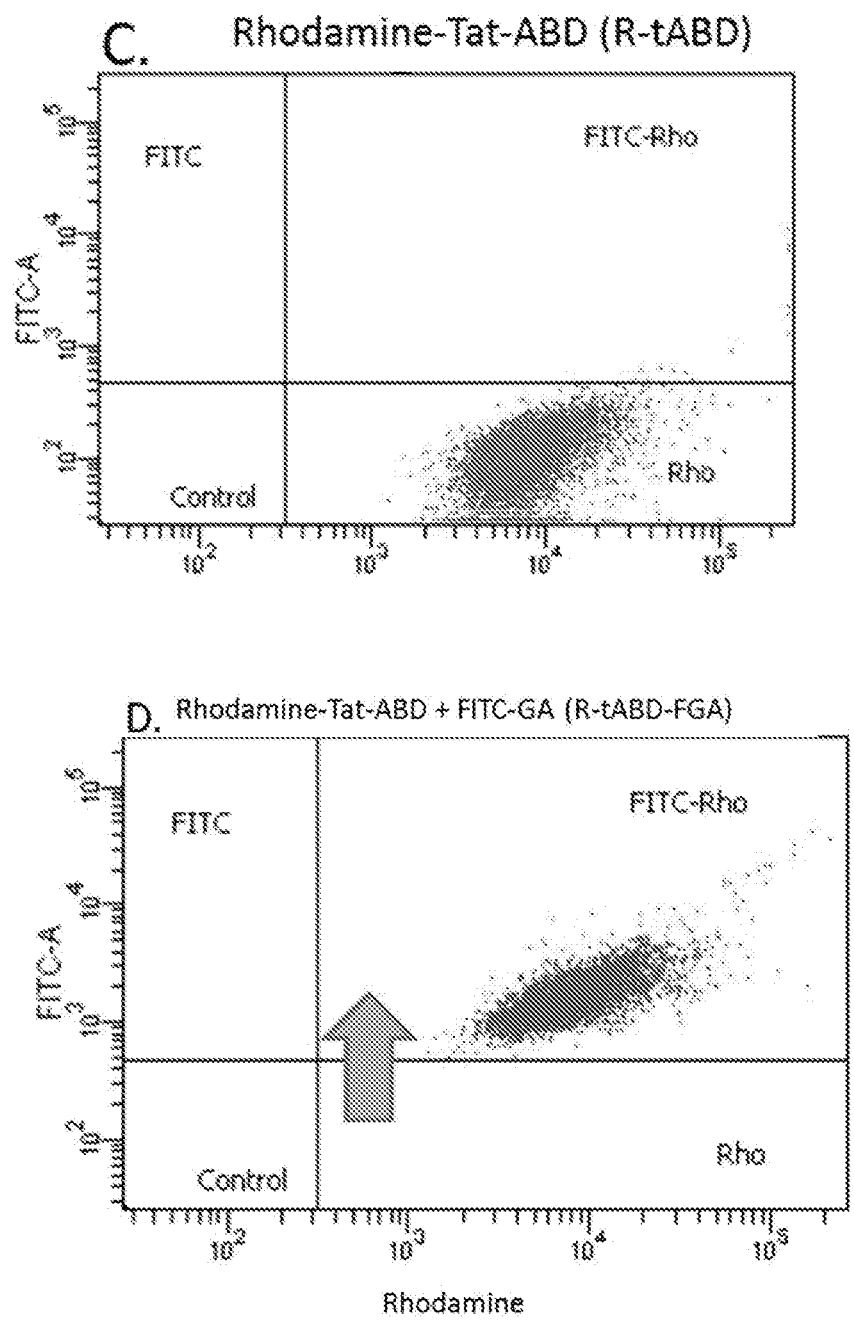
Figure 16E:
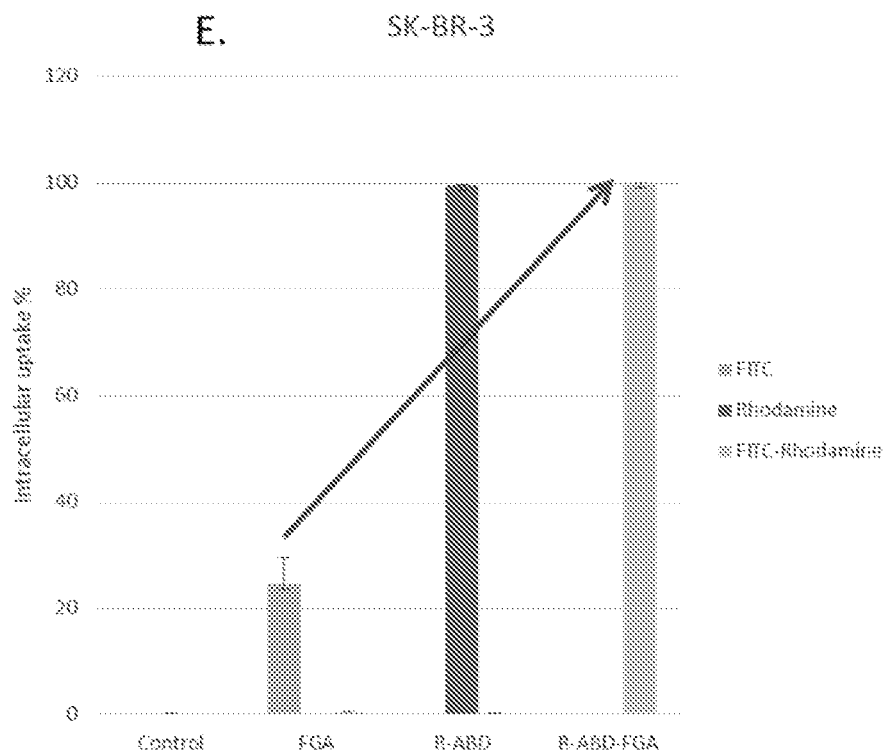

MDA-SK-BR-3 cell line: Intracellular uptake of FITC-GA was approximately 10% without the TAT-ABD protein (FIG. 16; FGA). TAT-ABD internalized into 100% of the cells (FIG. 16; R-tABD). TAT-ABD plus FITC-GA internalized into approximately 70% of the cells (FIG. 16; R-tABD-FGA). Approximately 30% cells were positive to solely Rhodamine.

Example 9: Targeted Anti-Cancer Activity of HER2-scFv-ABD-17-AAG

To verify the targeted anticancer activity of HER2-scFv-ABD-17-AAG, SKBR-3 (HER2+) and MDA-MB-231 (HER2−) cells were exposed to free-17-AAG (17A), free HER2-scFv-ABD protein (HA), or HER2-scFv-ABD-17-AAG (HA+17A). HA was mixed with 17-AAG at the molar ratio of 1:1 and incubated for 30 minutes at 4° C. prior to the contact with the cells. The cells were treated with 17-AAG or HA+17-AAG at different concentrations of 17-AAG ranging from 0.001 µg/ml to 1 ug/ml (final concentration). As a negative control, cells were exposed to equivalent amounts of free HA. After 5 hours of incubation, the cells were washed to remove unbound proteins and non-internalized 17-AAG and then further incubated for up to 72 hours. Cell viability was determined by MTT assay.

Figure 17:
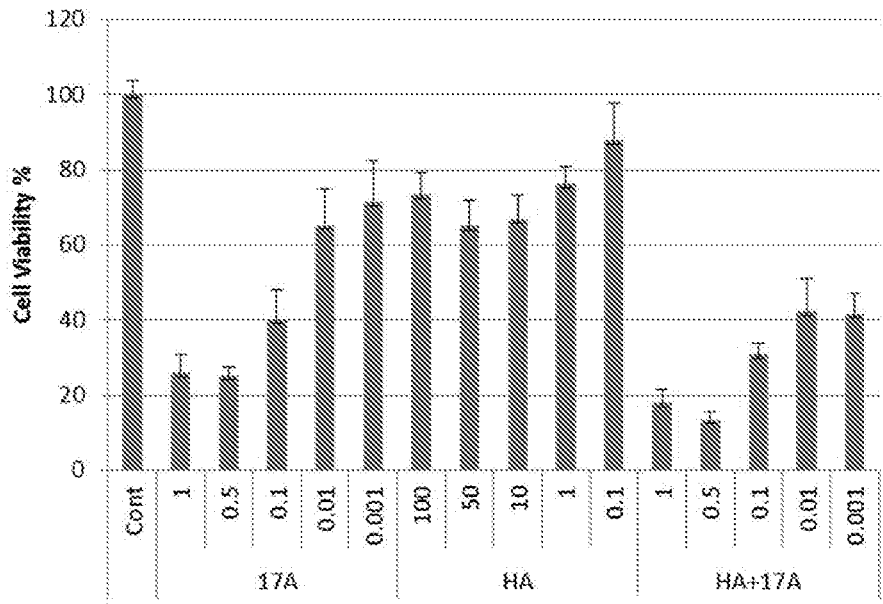
FIG. 17 shows that HER2-ABD/17-AAG (HA+17A) can improve the anti-cancer activity of 17-AAG in HER2-positive cancer cells (SKBr-3) compared to HER2-negative cancer cells (MDA-MB-231). Cells were exposed to free-17-AAG (17A), free HER2-scFv-ABD (HA), or HER2-scFv-ABD-17-AAG (HA+17A).
Figure 17:
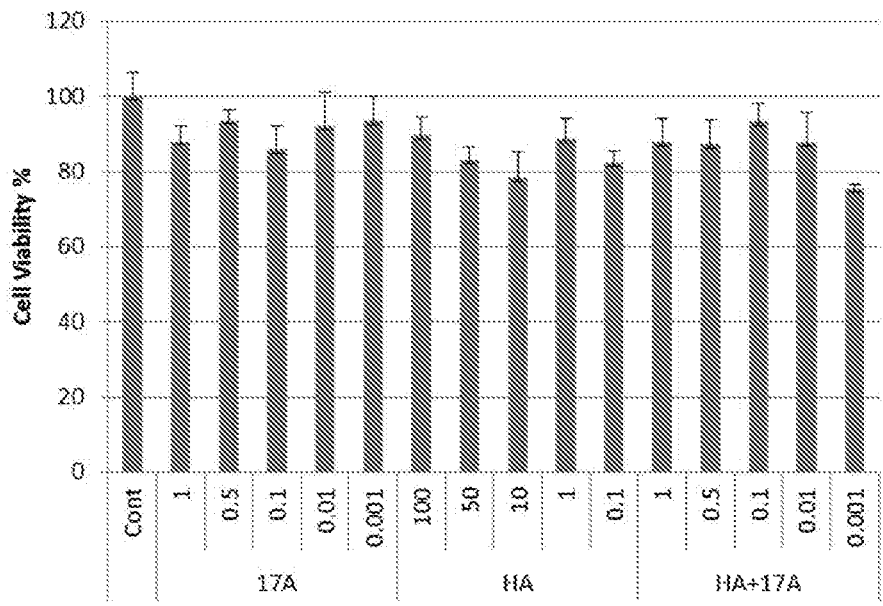

Exposure of the cells to HER2-scFv-ABD-17-AAG (HA+17A) increased the cytotoxicity of 17-AAG by facilitating uptake of 17-AAG into the target SKBR-3 cancer cells, whereas no difference in the cell viability was observed in MDA-MB-231 cells (FIG. 17). These results provide evidence that the formation of a bi-functional allosteric protein-drug molecule (e.g., HER2-ABD/17-AAG) can improve the anti-cancer activity of 17-AAG in HER2-positive cancer cells through specific binding and facilitated internalization of the therapeutic agent.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A bi-functional allosteric protein-drug molecule comprising a targeting moiety, one or more biological binding domains, and one or more therapeutic agents, wherein the therapeutic agent is allosterically bound to the biological binding domain, wherein the targeting moiety is an antibody, and wherein the biological binding domain comprises an ATP binding domain and/or a taxane binding domain, and wherein the antibody is capable of facilitating internalization of the bi-functional allosteric protein-drug molecule into a target cell.

2. The bi-functional allosteric protein-drug molecule of claim 1, wherein the antibody is a single chain antibody (scFv) or a Fab fragment.

3. The bi-functional allosteric protein-drug molecule of claim 1, wherein the antibody is human, chimeric or humanized or a biologically active variant thereof.

4. The bi-functional allosteric protein-drug molecule of claim 1, wherein the antibody is a monoclonal antibody or a polyclonal antibody.

5. The bi-functional allosteric protein-drug molecule of claim 2, wherein the scFv or Fab fragment specifically binds a growth factor receptor.

6. The bi-functional allosteric protein-drug molecule of claim 5, wherein the growth factor receptor is a member of the epidermal growth factor receptor (EGFR) family.

7. The bi-functional allosteric protein-drug molecule of claim 1, wherein the antibody is trastuzumab, panitumumab or cetuximab, or a biologically active variant thereof.

8. The bi-functional allosteric protein-drug molecule of claim 1, wherein the biological binding domain and the therapeutic agent are present in a ratio of 1:1 or 1:5 (binding domain:therapeutic).

9. The bi-functional allosteric protein-drug molecule of claim 1, wherein the biological binding domains are two or more.

10. The bi-functional allosteric protein-drug molecule of claim 1, wherein the therapeutic agent is an anti-cancer agent.

11. The bi-functional allosteric protein-drug molecule of claim 10, wherein the anti-cancer agent is a derivate of geldanamycin, a taxane or a HSP90 inhibitor.

12. The bi-functional allosteric protein-drug molecule of claim 11, wherein the geldanamycin derivative is 17-AAG or 17-DMAG.

13. The bi-functional allosteric protein-drug molecule of claim 11, wherein the taxane is paclitaxel or docetaxel.

14. The bi-functional allosteric protein-drug molecule of claim 11, wherein the HSP90 inhibitor is 17-AAG, geldanamycin, 17-DMAG, IPI-504, BIIB021, SNX-5422, STA-9090 or NVP-AUY922.

15. The bi-functional allosteric protein-drug molecule of claim 1, wherein the ATP binding domain comprises residues 9-232 of the N-terminus of HSP90.

16. The bi-functional allosteric protein-drug molecule of claim 1, wherein the taxane binding domain comprise β-tubulin.

17. A pharmaceutical composition comprising the bi-functional allosteric protein-drug molecule of claim 1 and a pharmaceutically acceptable carrier.

18. The pharmaceutical composition of claim 17, wherein the therapeutic agent is an anti-cancer agent and wherein the pharmaceutical composition is formulated for intravenous administration.

19. A method of treating a patient with cancer, the method comprising:
 (a) identifying a patient in need of treatment; and
 (b) administering to the patient a therapeutically effective amount of the pharmaceutical composition of claim 18.

* * * * *